(12) United States Patent
Burns, Jr. et al.

(10) Patent No.: US 7,766,887 B2
(45) Date of Patent: Aug. 3, 2010

(54) METHOD FOR MAKING REUSABLE DISPOSABLE ARTICLE

(75) Inventors: John Glasgow Burns, Jr., Springfield, OH (US); Clifford Theodore Papsdorf, Miami Township, OH (US); Darrell Ian Brown, Mason, OH (US); Stephen Lebeuf Hardie, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 877 days.

(21) Appl. No.: 11/598,308

(22) Filed: Nov. 13, 2006

(65) Prior Publication Data

US 2008/0114319 A1    May 15, 2008

(51) Int. Cl.
*A61F 13/15* (2006.01)
*A61F 13/20* (2006.01)
(52) U.S. Cl. .................................. 604/385.14
(58) Field of Classification Search ........... 604/386, 604/391, 393–402, 368–370, 372, 374, 378, 604/385.01, 385.14, 385.15, 385.19; 602/67–73; 2/400–409
See application file for complete search history.

(56) References Cited

U.S. PATENT DOCUMENTS

| | | | |
|---|---|---|---|
| 833,849 A | 10/1906 | Schiff |
| 1,695,109 A | 12/1928 | Kosloff |
| 1,893,745 A | 1/1933 | Josias |
| 2,468,445 A | 4/1949 | Hurst |
| 2,476,585 A | 7/1949 | Cohen |
| 2,530,647 A | 11/1950 | Buchler |
| 2,574,279 A | 11/1951 | Oberle |
| 2,688,328 A | 9/1954 | Marcus |
| 2,695,025 A | 11/1954 | Andrews |
| 2,788,786 A | 4/1957 | Dexter |
| 2,826,199 A | 3/1958 | Brandon |
| 2,832,346 A | 4/1958 | Morstad |
| 2,842,129 A | 7/1958 | Ernstorff |
| 2,868,205 A | 1/1959 | Epstein |

(Continued)

FOREIGN PATENT DOCUMENTS

CN    2073744 U    3/1991

(Continued)

OTHER PUBLICATIONS

International Search Report of PCT/IB2007/054527 dated Apr. 29, 2008.

(Continued)

*Primary Examiner*—Michele Kidwell
(74) *Attorney, Agent, or Firm*—Charles R. Matson

(57) ABSTRACT

A method for making absorbent articles such as diapers and training pants having a pocket for receiving a removable core component is provided. Absorbent articles having removable absorbent core components are further provided. A method for manufacturing an absorbent article comprises providing a wearer facing portion and a garment facing portion, and providing a first absorbent core component with either the wearer facing portion or the garment facing portion. The wearer facing portion and the garment facing portion are associated such that an openable chassis pocket is formed there between, the wearer facing portion and the garment facing portion being separable to create an access opening to the openable chassis pocket for receiving a replaceable absorbent core component.

8 Claims, 16 Drawing Sheets

U.S. PATENT DOCUMENTS

| | | |
|---|---|---|
| 3,050,063 A | 8/1962 | Margraf |
| 3,162,196 A | 12/1964 | Salk |
| RE26,151 E | 1/1967 | Duncan et al. |
| 3,306,293 A | 2/1967 | Marder et al. |
| 3,556,932 A | 1/1971 | Coscia et al. |
| 3,595,235 A | 7/1971 | Jespersen |
| 3,658,064 A | 4/1972 | Pociluyko |
| 3,661,875 A | 5/1972 | Sieja |
| 3,771,524 A | 11/1973 | Ralph |
| 3,848,594 A | 11/1974 | Buell |
| 3,860,003 A | 1/1975 | Buell |
| 3,886,941 A | 6/1975 | Duane et al. |
| 3,911,173 A | 10/1975 | Sprague, Jr. |
| 3,918,433 A | 11/1975 | Fuisz |
| 3,926,189 A | 12/1975 | Taylor |
| 4,019,517 A | 4/1977 | Glassman |
| 4,022,210 A | 5/1977 | Glassman |
| 4,062,817 A | 12/1977 | Westerman |
| 4,072,150 A | 2/1978 | Glassman |
| 4,076,663 A | 2/1978 | Masuda et al. |
| 4,081,301 A | 3/1978 | Buell |
| 4,093,776 A | 6/1978 | Aoki et al. |
| 4,257,418 A | 3/1981 | Hessner |
| 4,260,443 A | 4/1981 | Lindsay et al. |
| 4,265,245 A | 5/1981 | Glassman |
| 4,326,302 A | 4/1982 | Lowe et al. |
| 4,467,012 A | 8/1984 | Pedersen et al. |
| 4,496,360 A | 1/1985 | Joffe et al. |
| 4,515,595 A | 5/1985 | Kievit et al. |
| 4,560,381 A | 12/1985 | Southwell |
| 4,573,986 A | 3/1986 | Minetola et al. |
| 4,578,073 A | 3/1986 | Dysart et al. |
| 4,597,760 A | 7/1986 | Buell |
| 4,597,761 A | 7/1986 | Buell |
| 4,605,403 A | 8/1986 | Tucker |
| 4,610,678 A | 9/1986 | Weisman et al. |
| 4,615,695 A | 10/1986 | Cooper |
| 4,625,001 A | 11/1986 | Tsubakimoto et al. |
| 4,654,039 A | 3/1987 | Brandt et al. |
| 4,666,983 A | 5/1987 | Tsubakimoto et al. |
| 4,695,278 A | 9/1987 | Lawson |
| 4,699,619 A | 10/1987 | Bernardin |
| 4,710,188 A | 12/1987 | Runeman |
| 4,715,918 A | 12/1987 | Lang |
| 4,734,478 A | 3/1988 | Tsubakimoto et al. |
| 4,756,709 A | 7/1988 | Stevens |
| 4,770,656 A | 9/1988 | Proxmire et al. |
| 4,773,903 A | 9/1988 | Weisman et al. |
| D298,566 S | 11/1988 | Runeman |
| 4,785,996 A | 11/1988 | Ziecker et al. |
| 4,808,178 A | 2/1989 | Aziz et al. |
| 4,816,025 A | 3/1989 | Foreman |
| 4,822,453 A | 4/1989 | Dean et al. |
| 4,826,499 A | 5/1989 | Ahr |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,851,069 A | 7/1989 | Packard et al. |
| 4,872,871 A | 10/1989 | Proxmire et al. |
| 4,888,093 A | 12/1989 | Dean et al. |
| 4,892,598 A | 1/1990 | Stevens et al. |
| 4,898,642 A | 2/1990 | Moore et al. |
| 4,923,454 A | 5/1990 | Seymour et al. |
| 4,938,756 A | 7/1990 | Salek |
| 4,950,264 A | 8/1990 | Osborn, III |
| 4,961,736 A | 10/1990 | McCloud |
| 4,964,857 A | 10/1990 | Osborn |
| 4,964,860 A | 10/1990 | Gipson et al. |
| 4,968,312 A | 11/1990 | Khan |
| 4,988,344 A | 1/1991 | Reising et al. |
| 4,988,345 A | 1/1991 | Reising |
| 4,994,037 A | 2/1991 | Bernardin |
| 5,009,650 A | 4/1991 | Bernardin |
| 5,009,653 A | 4/1991 | Osborn, III |
| 5,019,068 A | 5/1991 | Perez et al. |
| 5,061,259 A | 10/1991 | Goldman et al. |
| 5,069,672 A | 12/1991 | Wippler et al. |
| 5,098,423 A | 3/1992 | Pieniak et al. |
| 5,102,597 A | 4/1992 | Roe et al. |
| 5,128,082 A | 7/1992 | Makoui |
| 5,137,537 A | 8/1992 | Herron et al. |
| 5,141,505 A | 8/1992 | Barrett |
| 5,147,345 A | 9/1992 | Young et al. |
| 5,149,335 A | 9/1992 | Kellenberger et al. |
| 5,167,655 A | 12/1992 | McCoy |
| 5,176,668 A | 1/1993 | Bernardin |
| 5,181,915 A | 1/1993 | Smith |
| 5,188,624 A | 2/1993 | Young, Sr. et al. |
| 5,207,662 A | 5/1993 | James |
| 5,207,663 A | 5/1993 | McQueen |
| 5,217,445 A | 6/1993 | Young et al. |
| 5,236,428 A | 8/1993 | Zajaczkowski |
| 5,260,345 A | 11/1993 | DesMarais et al. |
| 5,268,224 A | 12/1993 | DesMarais et al. |
| 5,318,554 A | 6/1994 | Young et al. |
| 5,324,561 A | 6/1994 | Rezai et al. |
| 5,325,543 A | 7/1994 | Allen |
| 5,358,500 A | 10/1994 | LaVon et al. |
| 5,360,419 A | 11/1994 | Chen et al. |
| 5,360,422 A | 11/1994 | Brownlee et al. |
| 5,383,867 A | 1/1995 | Klinger |
| 5,387,207 A | 2/1995 | Dyer et al. |
| 5,401,266 A | 3/1995 | Runeman et al. |
| 5,405,342 A | 4/1995 | Roessler et al. |
| 5,409,476 A | 4/1995 | Coates |
| 5,458,591 A | 10/1995 | Roessler et al. |
| 5,476,457 A | 12/1995 | Roessler et al. |
| 5,486,168 A | 1/1996 | Runeman et al. |
| 5,531,728 A | 7/1996 | Lash |
| 5,549,589 A | 8/1996 | Horney et al. |
| 5,549,775 A | 8/1996 | Odorzynski |
| 5,550,167 A | 8/1996 | DesMarais |
| 5,556,393 A | 9/1996 | Rönnberg |
| 5,562,646 A | 10/1996 | Goldman et al. |
| 5,563,179 A | 10/1996 | Stone et al. |
| 5,569,229 A | 10/1996 | Rogers |
| 5,599,335 A | 2/1997 | Goldman et al. |
| 5,613,959 A | 3/1997 | Roessler et al. |
| 5,636,387 A | 6/1997 | Lundy |
| 5,650,222 A | 7/1997 | DesMarais et al. |
| 5,667,503 A | 9/1997 | Roe et al. |
| 5,778,110 A | 7/1998 | Furuya |
| 5,800,416 A | 9/1998 | Seger et al. |
| 5,817,081 A | 10/1998 | LaVon et al. |
| 5,827,253 A | 10/1998 | Young et al. |
| 5,843,055 A | 12/1998 | Seger |
| 5,843,065 A | 12/1998 | Wyant |
| 5,906,602 A | 5/1999 | Weber et al. |
| 5,941,863 A | 8/1999 | Guidotti et al. |
| 6,015,935 A | 1/2000 | LaVon et al. |
| 6,083,210 A | 7/2000 | Young et al. |
| 6,229,061 B1 | 5/2001 | Dragoo et al. |
| 6,336,923 B1 | 1/2002 | Fujioka et al. |
| 6,443,933 B1 | 9/2002 | Suzuki et al. |
| 6,623,466 B1 | 9/2003 | Richardson |
| 6,689,114 B2 | 2/2004 | Bouchard et al. |
| 6,766,817 B2 | 7/2004 | da Silva |
| 6,793,649 B1 | 9/2004 | Fujioka et al. |
| 6,918,404 B2 | 7/2005 | da Silva |
| 6,989,005 B1 | 1/2006 | LaVon et al. |
| 6,989,006 B2 | 1/2006 | LaVon et al. |
| 7,066,586 B2 | 6/2006 | da Silva |
| 7,175,613 B2 * | 2/2007 | Sugiyama et al. ...... 604/385.14 |

| | | | | | | |
|---|---|---|---|---|---|---|
| 7,285,255 | B2 | 10/2007 | Kadlec et al. | GB | 2 269 998 | 3/1994 |
| 2002/0013566 | A1 | 1/2002 | Chappell et al. | GB | 2 295 321 A | 5/1996 |
| 2002/0058921 | A1 | 5/2002 | Sigl | JP | 04161152 | 4/1992 |
| 2002/0091368 | A1 | 7/2002 | LaVon et al. | JP | 1993-86314 | 11/1993 |
| 2002/0112982 | A1 | 8/2002 | Stagray et al. | JP | 06-121812 | 5/1994 |
| 2002/0143311 | A1 | 10/2002 | Brisebois | WO | WO 89/11843 | 12/1989 |
| 2002/0143316 | A1 | 10/2002 | Sherrod et al. | WO | WO 91/10413 | 7/1991 |
| 2003/0220623 | A1 | 11/2003 | Sugiyama et al. | WO | WO 91/16871 | 11/1991 |
| 2004/0024379 | A1 | 2/2004 | LaVon et al. | WO | WO 94/24973 | 11/1994 |
| 2004/0030314 | A1 | 2/2004 | LaVon et al. | WO | WO 95/17870 | 7/1995 |
| 2004/0039361 | A1 | 2/2004 | LaVon et al. | WO | WO 01/60300 A1 | 8/2001 |
| 2005/0103436 | A1 | 5/2005 | Otsubo et al. | | | |

FOREIGN PATENT DOCUMENTS

| | | |
|---|---|---|
| EP | 0 319 314 A2 | 6/1989 |
| GB | 493819 | 10/1938 |
| GB | 734994 | 8/1955 |
| GB | 1 411 087 | 10/1975 |
| GB | 2 042 342 | 9/1980 |

OTHER PUBLICATIONS

U.S. Appl. No. 11/588,135, filed Oct. 26, 2006, Lavon.
U.S. Appl. No. 11/588,134, filed Oct. 26, 2006, Lavon, et al.
U.S. Appl. No. 11/598,462, filed Nov. 13, 2006, Beck, et al.
U.S. Appl. No. 11/598,406, filed Nov. 13, 2006, Beck, et al.

* cited by examiner

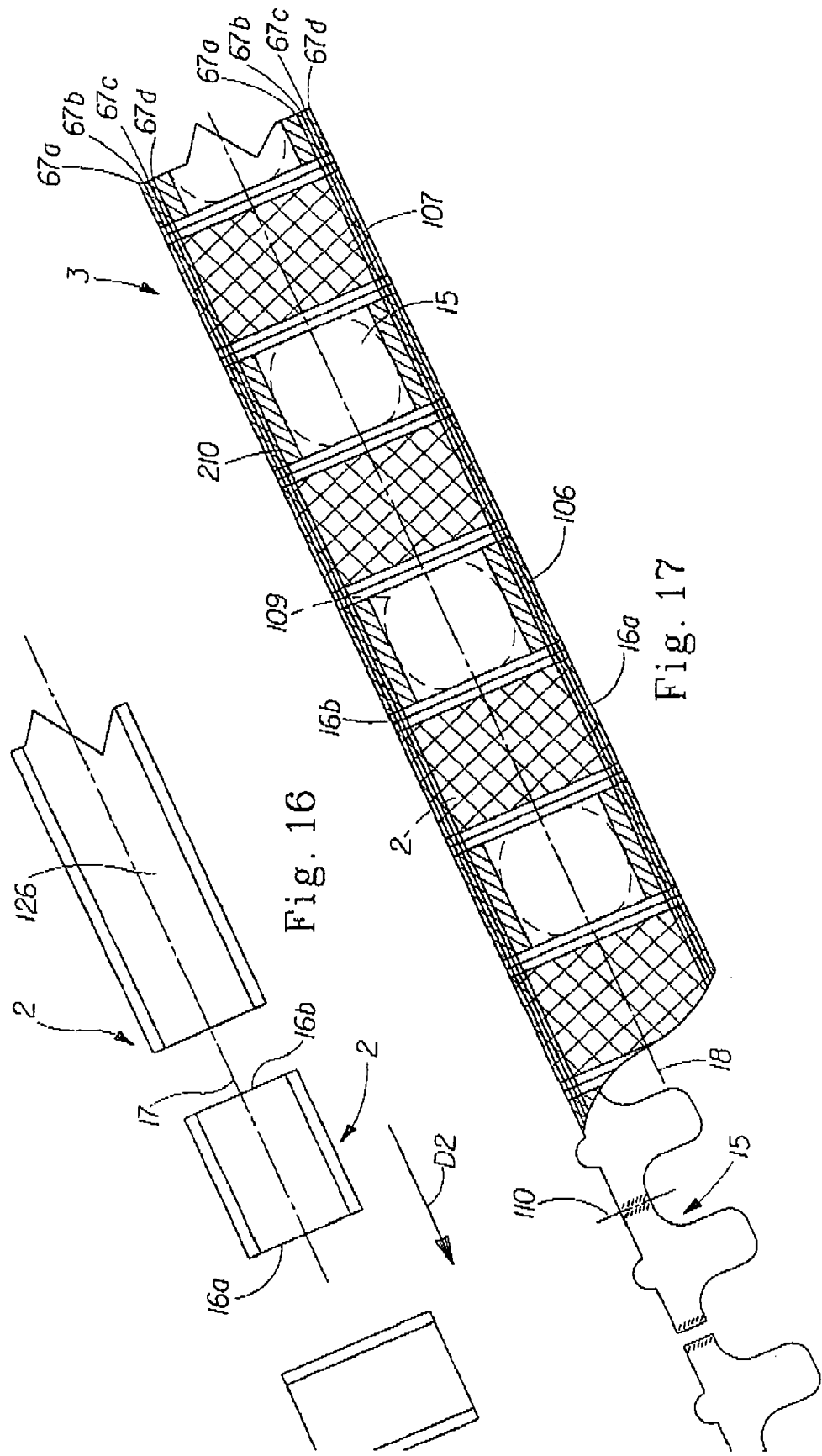

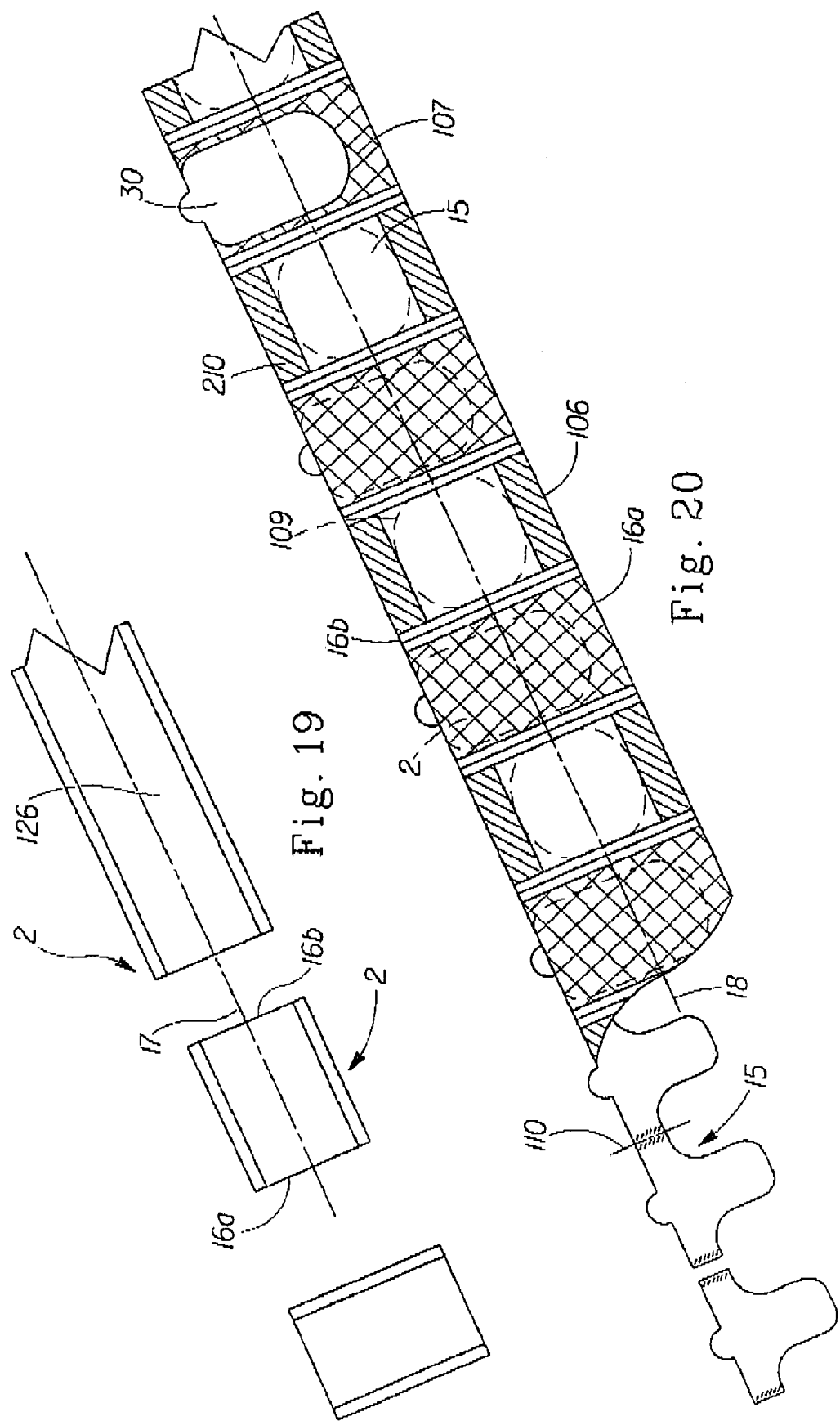

METHOD FOR MAKING REUSABLE DISPOSABLE ARTICLE

FIELD OF THE INVENTION

The present invention relates to a method for making absorbent articles such as diapers and training pants. More particularly, the present invention relates to a method for making absorbent articles such as diapers and training pants having an openable chassis pocket for receiving a replaceable absorbent core component. The invention further relates to a method for making absorbent articles having an openable chassis pocket wherein a replaceable absorbent core component is disposed.

BACKGROUND OF THE INVENTION

Infants and other incontinent individuals wear absorbent articles such as diapers, training pants and the like to absorb and retain urine and other body exudates. Absorbent articles function both to contain the discharged materials and to isolate these materials from the body of the wearer and from the wearer's garments and bed clothing. Disposable absorbent articles having many different basic designs are described, for example, in U.S. Pat. No. Re. 26,151 and U.S. Pat. No. 3,860,003. Typically, absorbent articles have an absorbent core for absorbing urine and other body exudates. Some of these articles tend to store absorbed fluids in a discharge region of the article. This discharge region is positioned generally within the portion of the article that fits in the wearer's crotch region when worn. A contributing factor to discomfort of the article to the wearer is the inability of the article to effectively transport discharged fluids.

In addition, many absorbent articles, such as catamenial pads, adult incontinent products, training pants and diapers, may leak upon repeated discharges of liquid, even if the prior liquid discharges have been effectively absorbed. Leakage due to repeated discharges is especially prevalent during the night, when users commonly experience multiple discharges before the absorbent article is changed. One factor that restricts the ability of many absorbent articles to handle multiple discharges of liquid is the absorbent core's limitations in transporting discharged liquid away from the discharge region once the absorbent capacity of that region has been reached. Thus, the overall performance of the absorbent article may be limited by the inability to transport the liquid to the farthest reaches of the absorbent core.

An example of an absorbent material capable of providing capillary liquid transport is open-celled polymeric foam. Appropriately made open-celled polymeric foams can provide features of capillary liquid acquisition, transport, and storage for use in high performance absorbent cores for absorbent articles such as diapers. Shaped or contoured absorbent cores made from such open-celled foam materials are disclosed in U.S. Pat. No. 5,147,345. The '345 patent's absorbent core includes both a liquid acquisition/distribution member and a liquid storage/redistribution member. The liquid acquisition/distribution member is positioned within the absorbent article in such a way as to receive or contact aqueous bodily liquid which has been discharged into the absorbent article by the wearer of the article. The liquid storage/redistribution member, in turn, is positioned within the article to be in capillary liquid communication with the liquid acquisition/distribution member.

Absorbent cores providing the absorbent characteristics of the '345 patent in an exemplary multi-piece configuration are disclosed in U.S. Pat. No. 5,906,602, which describes shaped absorbent cores having a front panel and a back panel in capillary liquid communication with a center section. The center section includes material generally suitable for liquid acquisition/distribution, while the front and back panels include material generally suitable for liquid storage/redistribution.

Despite advances in absorbent articles and in liquid handling absorbent core materials, absorbent articles having multiple absorbent core components as well as those having unitary absorbent cores generally remain designed for single use wear. Once the storage/redistribution member is saturated with bodily discharges, such as urine, the entire absorbent article is generally discarded and replaced. Often parts of the absorbent article are still usable, and except for being unitary with the absorbent core, these parts could be used further. In addition to the added cost and waste associated with discarding reusable materials, it is often inconvenient to remove and replace the entire absorbent article when absorbent core components are saturated.

Absorbent articles having removable absorbent inserts are disclosed, for example, in U.S. Pat. No. 4,597,761, which discloses a disposable absorbent insert for use inside an overgarment such as a conventional reusable diaper, or a disposable diaper. Once the absorbent insert becomes saturated it may be removed and discarded. The absorbent article may then be reused with a fresh absorbent insert. However, because the absorbent insert is removable only from the body side of the article, the absorbent article is removed from the wearer in order to remove the insert. Therefore, the removal of the absorbent insert is often inconvenient and time consuming.

It would be advantageous to provide an absorbent article that provides improved fit and wearer comfort, even after the article is wetted with body fluids, such as by reducing the relative amount of fluid retained in the article's crotch region. It would be further advantageous to provide an absorbent article which has reduced bulk in the crotch region in both the dry and wet states. Accordingly, it would be desirable to provide an absorbent article having an openable chassis pocket for receiving a replaceable absorbent core component wherein the replaceable absorbent core component can be replaced without having to remove the absorbent article from the wearer. It would also be advantageous to provide a method of manufacturing such an absorbent article.

SUMMARY OF THE INVENTION

A method for making absorbent articles such as diapers and training pants having an openable chassis pocket for receiving a replaceable absorbent core component is provided.

In accordance with one embodiment, the method of manufacturing of an absorbent article comprises providing a first absorbent core component disposed between a wearer facing portion and a garment facing portion and associating the wearer facing portion with the garment facing portion. Association of the wearer facing portion and the garment facing portion is such that an openable chassis pocket is formed there between, the wearer facing portion and the garment facing portion being separable to create an access opening to the openable chassis pocket for receiving a replaceable absorbent core component.

In accordance with another embodiment of the present invention the method of manufacturing of an absorbent article, comprises providing a wearer facing portion and a garment facing portion. The wearer facing portion includes a topsheet and has a first direction of travel. The garment facing portion includes a backsheet and has a second direction of travel. The method further comprises providing a first absorbent core component, the first absorbent core component associated with one of the garment facing portion or the wearer facing portion. The method further comprises changing the wearer facing portion from the first direction of travel to the second direction of travel. The method further comprises associating the wearer facing portion with the garment facing portion such that an openable chassis pocket if formed there between, the wearer facing portion and the garment facing portion being separable to create an access opening to the openable chassis pocket for receiving a replaceable absorbent core component.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature, and not as restrictive.

BRIEF DESCRIPTION OF THE DRAWINGS

While the specification concludes with claims particularly pointing out and distinctly claiming the subject matter which is regarded as forming the present invention, it is believed that the invention will be better understood from the following description, which is taken in conjunction with the accompanying drawings in which like designations are used to designate substantially identical elements, and in which:

FIG. 16 illustrates a plan view of a core and chassis combined on a process carrier web without a packet in accordance with one embodiment.

FIG. 17 illustrates a plan view of a core and chassis combined on a process carrier web without a packet in accordance with another embodiment.

FIG. 19 illustrates a plan view of a core and chassis combined on a process carrier web with a packet in accordance with one embodiment.

FIG. 20 illustrates a plan view of a core and chassis combined on a process carrier web with a packet in accordance with another embodiment.

DETAILED DESCRIPTION OF THE INVENTION

Figure 1A:
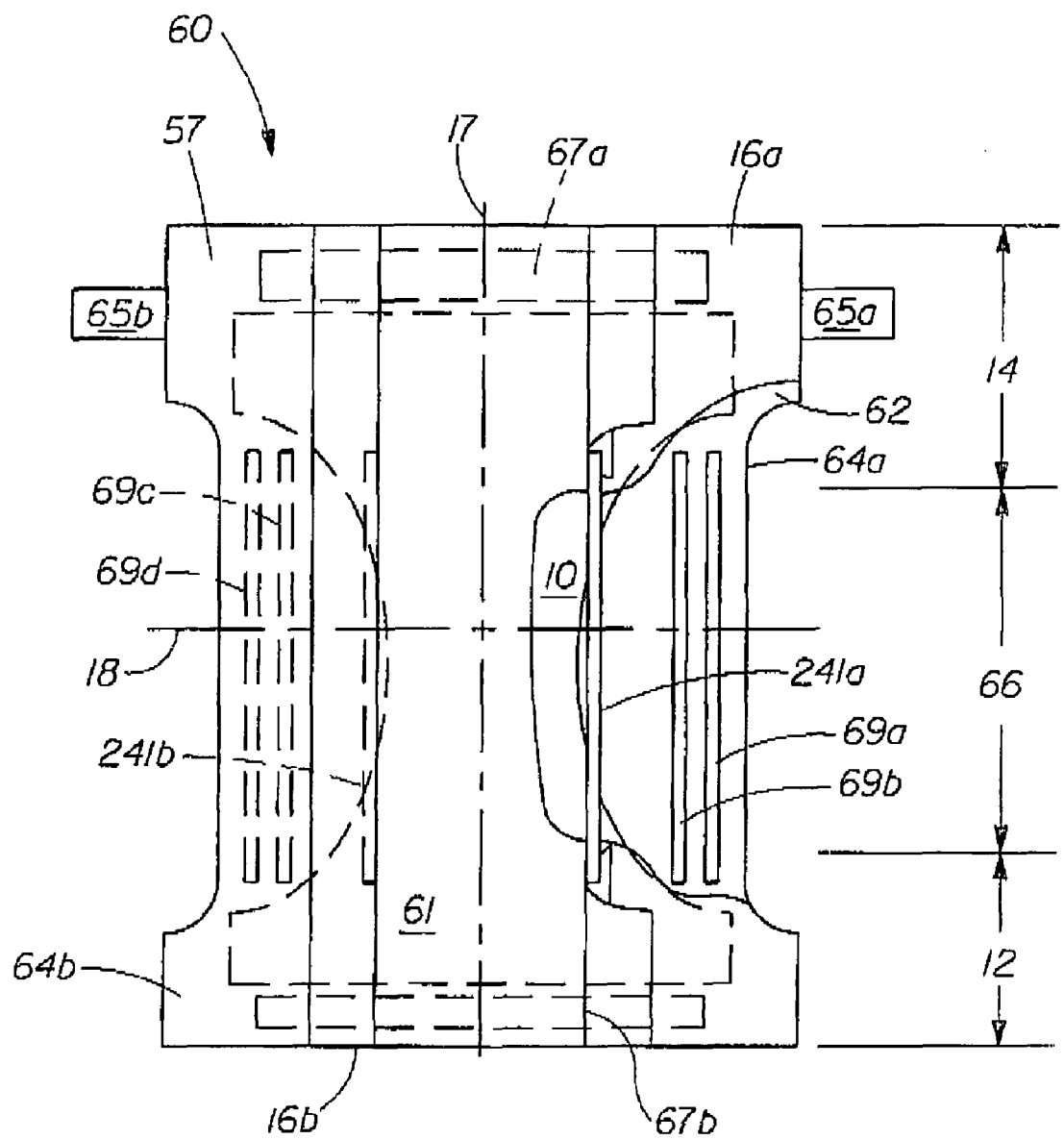
FIG. 1a illustrates a plan view of a diaper in accordance with one embodiment.

A method for making absorbent articles such as diapers and training pants having an openable chassis pocket for receiving a replaceable absorbent core component is provided. Absorbent articles having replaceable absorbent core components are further provided.

The following definitions of terms may be useful for understanding the disclosure of the present invention.

As used herein, the term longitudinal axis refers to an axis of the absorbent article that extends from the midpoint of a first waist end edge of the article in a first waist region through the crotch region to the midpoint of a second waist end edge of the article in a second waist region (and corresponds to the length of the article at the midpoint).

As used herein, the term lateral axis refers to an axis of the absorbent article that extends from the midpoint of a first longitudinal side edge of the article in the crotch region through the midpoint of a second longitudinal side edge of the absorbent article in the crotch region (and corresponds to the width of the finished article at the midpoint).

As used herein, the term "absorbent article" refers to a device that absorbs and contains bodily exudates by means of an absorbent core, and, more specifically, a device which is placed against or in proximity to the body of a wearer to absorb and contain the various exudates discharged from the body. One embodiment of an absorbent article of the present invention is the disposable absorbent article, or diaper, shown in the drawing figures. It should be understood, however, that the present invention is also applicable to other absorbent articles such as incontinence briefs, incontinence undergarments, diaper holders and liners, training pants, pull-on diapers, and the like.

As used herein, the term "absorbent core component" refers to a structural constituent of an absorbent core, e.g., a piece of an absorbent core, such as one of multiple pieces in a multi-piece absorbent core.

As used herein, the term "absorbent insert" refers to a device adapted for insertion into an absorbent article and to serve as an absorbent core component when so inserted. A replaceable absorbent core component is an absorbent insert, the latter term being especially descriptive when referring to the device alone.

As used herein, the term "chassis" refers to a foundational constituent of an absorbent article upon which the remainder of the structure of the article is built up or overlaid, e.g., in a diaper, the structural elements that give the diaper the form of briefs or short pants when configured for wearing, such as a backsheet, a topsheet, or a combination of a topsheet and a backsheet.

As used herein, the term "diaper" refers to an absorbent article generally worn by infants and incontinent persons about the lower torso of the wearer.

As used herein, the term "disposable" is used to describe absorbent articles that are not intended to be laundered or otherwise restored or reused as an absorbent article after use, i.e., that are intended to be discarded after a single use and, optionally, to be recycled, composted or otherwise disposed of in an environmentally compatible manner. Note that, as described in this disclosure, a single use of a chassis and a non-removable core component may correspond to several uses and replacements of replaceable core components.

As used herein, the term "capillary liquid communication" refers to the flow of a liquid from one absorbent element to another absorbent element by capillary transport. Also, a term used to describe a structural disposition of absorbent elements in which the flow of a liquid from one of the absorbent elements to the other occurs through capillary transport of the liquid, generally involving either the direct face-to-face contact of the absorbent elements with each other, the direct face-to-face contact of each of the absorbent elements with a hydrophilic intermediate layer providing capillary conduction of the liquid from one absorbent element to the other, or the protrusion of the fibers of a fibrous absorbent element through a porous and/or permeable intermediate layer into contact with the other absorbent element.

As used herein, "join," "joined," "joining," and similar terms refer to configurations wherein an element is directly secured to another element by affixing the element directly to the other element, as well as configurations wherein the element is indirectly secured to the other element by affixing the element to an intermediate member or members which in turn is or are affixed to the other element.

As used herein, "replaceable" describes a component of an absorbent article that can be replaced, such as a component that can be removed and for which a like component can be substituted in place of the removed component, e.g., a replaceable absorbent core component or absorbent insert.

As used herein, the term "absorbent core" is used to describe the portions (e.g., layers) of an absorbent article that function to acquire, distribute, transfer, store, and/or redistribute fluid. Acquisition materials include material whose primary function is to acquire, and optionally then relinquish, fluids. Such materials include acquisition layers, topsheet materials, transfer layers, flow control modules, wrap tissues, or nonwoven sheets designed to prevent migration of hydrogel forming polymers, etc. As used herein, the term "distribution material" refers to the absorbent core material(s) whose primary function is to absorb and distribute/redistribute fluid to points away from the point of initial fluid loading. As used herein, the term "storage material" refers to the absorbent core material that retains a majority of the fluid retained, on a weight basis. It should be understood that the terms "distribution material" and "storage material" are not mutually exclusive. In certain embodiments, a single material may function to provide both fluid distribution and fluid storage.

As used herein, the term "front" refers to the portion of an article or absorbent core that is intended to be positioned proximate the front of a wearer. The term "rear" refers to the portion of an article or absorbent core that is intended to be positioned proximate the back of the wearer. As such, use of the relative term "in front of" means a position in the article or core more toward the front of the article or core, while the term "behind" means a position in the article or core more toward the rear of the article or core.

As used herein, the term "z-dimension" refers to the dimension orthogonal to the length and width of the member, core or article. The z-dimension corresponds generally to the thickness of the member, core, or article. As used herein, the term "x-y dimension" refers to the plane orthogonal to the thickness of the member, core, or article. The x- and y-dimensions correspond generally to the width and length, respectively, of the member, core, or article.

As used herein, the term "layers" refers to identifiable components of the absorbent structure, and any structure referred to as a "layer" may actually comprise a laminate or combination of several sheets or webs of materials as hereinafter described. As used herein, the term "layer" includes the terms "layers" and "layered." The term "upper" refers to the layer of the absorbent core that is nearest to and faces the article topsheet; conversely, the term "lower" refers to the layer of the absorbent core that is nearest to and faces the article backsheet. The various members, layers, and structures of absorbent articles may or may not be generally planar in nature, and may be shaped or profiled in any desired configuration.

As used herein, the term "wearer facing portion" refers to the elements of the chassis that form the inner surface of the absorbent article, such as the topsheet, the inner leg cuffs, the outer leg cuffs, the side panels, waistbands, waist shields, fasteners, etc., when such elements are present.

As used herein, the term "garment facing portion" refers to the elements of the chassis that form the outer surface of the absorbent article, such as the backsheet, the side panels, waistbands, outer leg cuffs, the fasteners, and the like, when such elements are present.

Figure 1B:
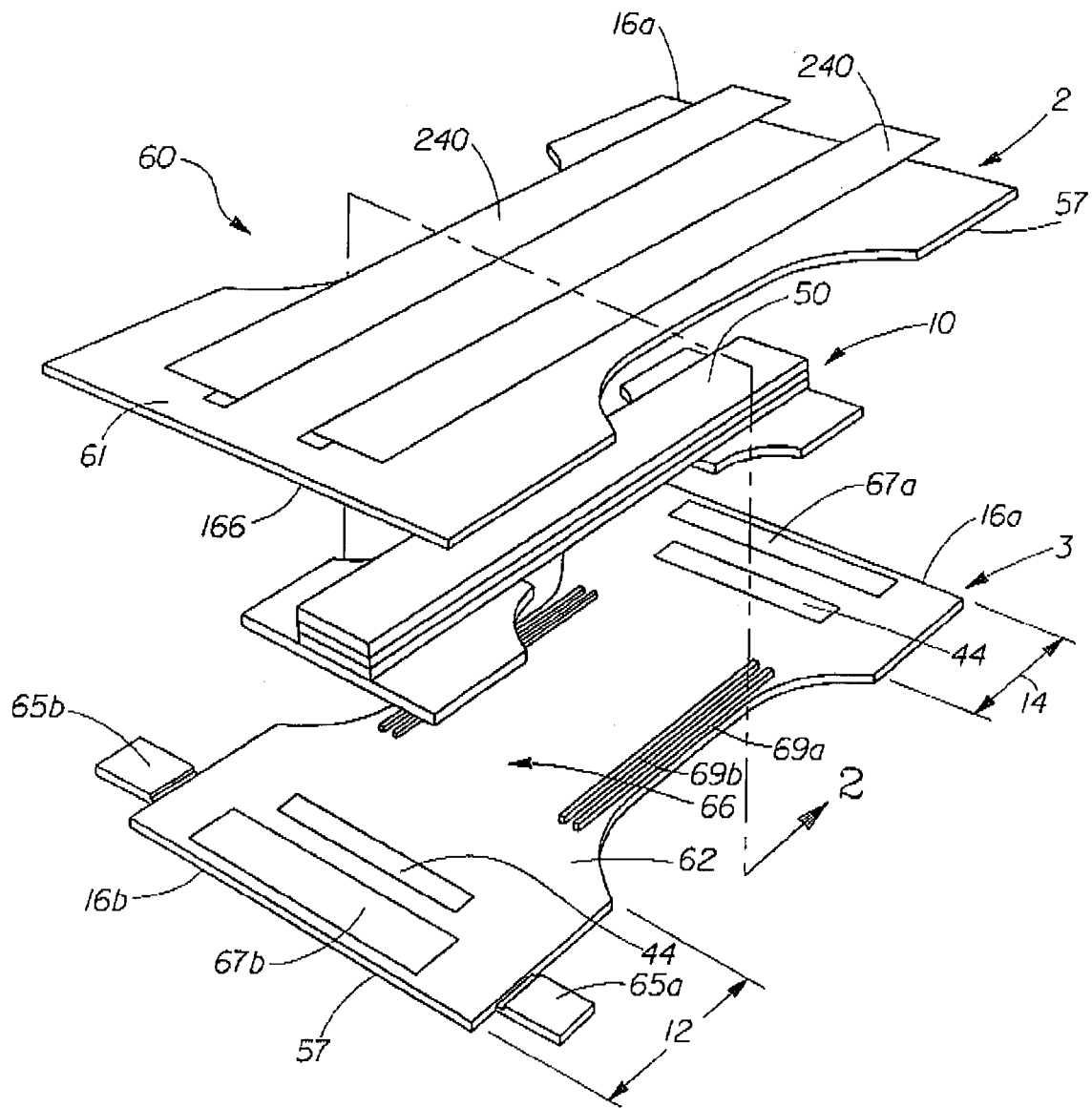
FIG. 1b illustrates an exploded view of a diaper in accordance with one embodiment.

As described below in detail, a method for manufacturing absorbent articles suitable for absorbing and retaining aqueous bodily liquids is provided. FIGS. 1a and 1b illustrate a diaper such as may be used with the present teachings. FIG. 1a illustrates a plan view of a diaper 60. FIG. 1b illustrates an exploded view of a diaper 60 in a flat-out, uncontracted state (i.e., with any elastic-induced contraction removed). As shown, the absorbent articles generally include a topsheet 61, a backsheet 62, and an absorbent core 10 positioned between the topsheet 61 and the backsheet 62. The backsheet 62 may comprise an impermeable layer and a nonwoven web in the form of a laminate. One example of a suitable impermeable layer is a polyolefin film layer. As discussed more fully below in reference to FIGS. 2-4, the absorbent core 10 may include at least one replaceable absorbent core component 20 and/or 30 disposed in capillary liquid communication with at least one additional absorbent core component such as a non-removable, absorbent core component 50. The diaper 60 includes a wearer facing portion 2 and a garment facing portion 3.

As shown in FIG. 1a, the diaper 60 has a front waist region 12, a back waist region 14, a crotch region 66, and a periphery 57 that is defined by the outer edge of backsheet 62 and that has longitudinally opposed waist end edges 16a and 16b and laterally opposed side edges 64a and 64b, left side edge and right side edge respectively. The waist regions 12, 14 comprise the upper portions of the diaper 60 that, when worn, encircle the waist of the wearer. The crotch region 66 is that portion of the diaper 60 between waist regions 12 and 14, and comprises that portion of the diaper 60 that, when worn, is positioned between the legs of the wearer and covers the lower torso of the wearer. Thus, the crotch region 66 may define the area of typical liquid deposition for a diaper 60 or other disposable absorbent article.

Figure 14A:
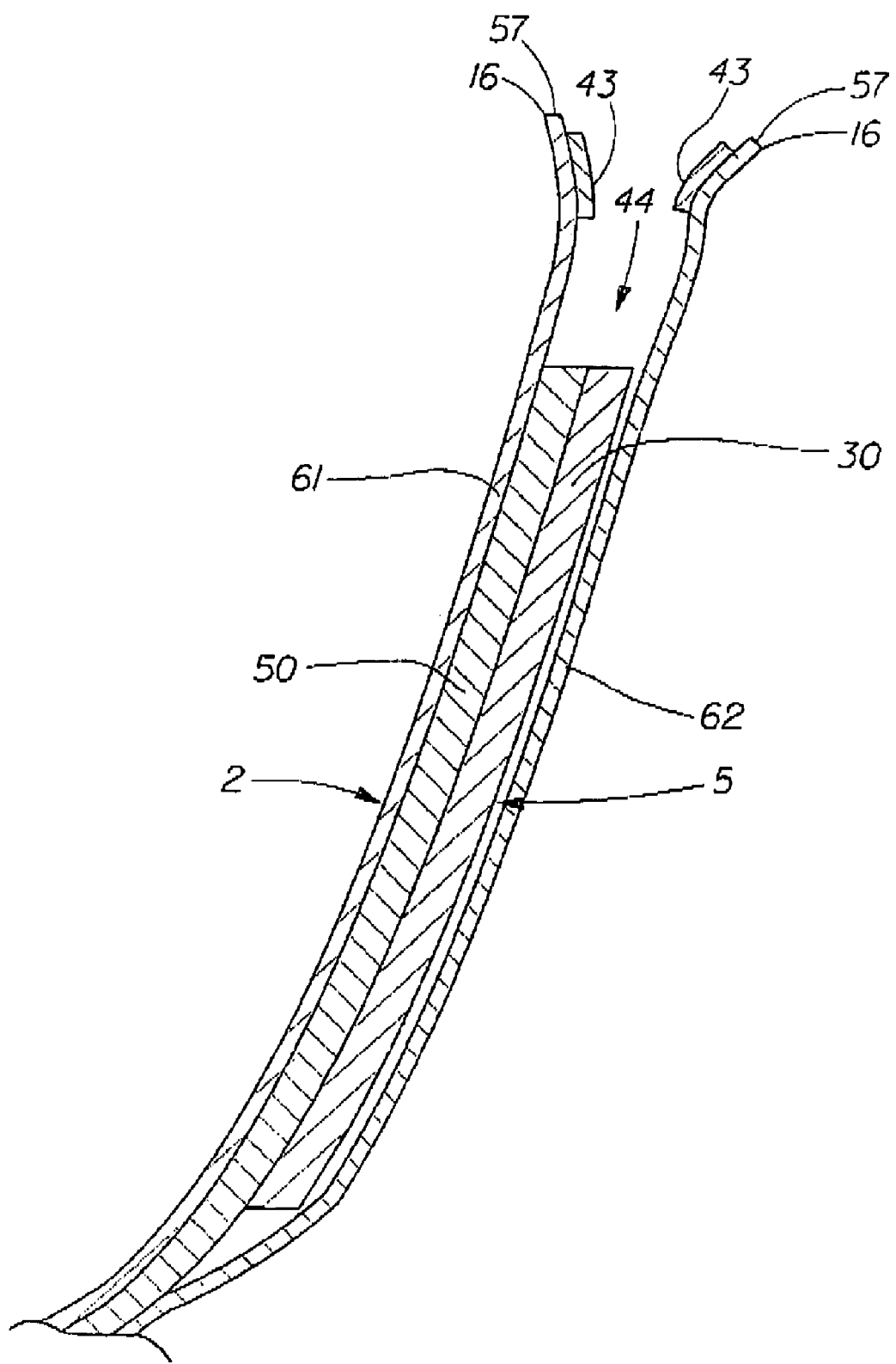
FIG. 14a illustrates a side cross sectional view of a diaper having a chassis opening at the top waist edge in accordance with one embodiment.
Figure 14B:
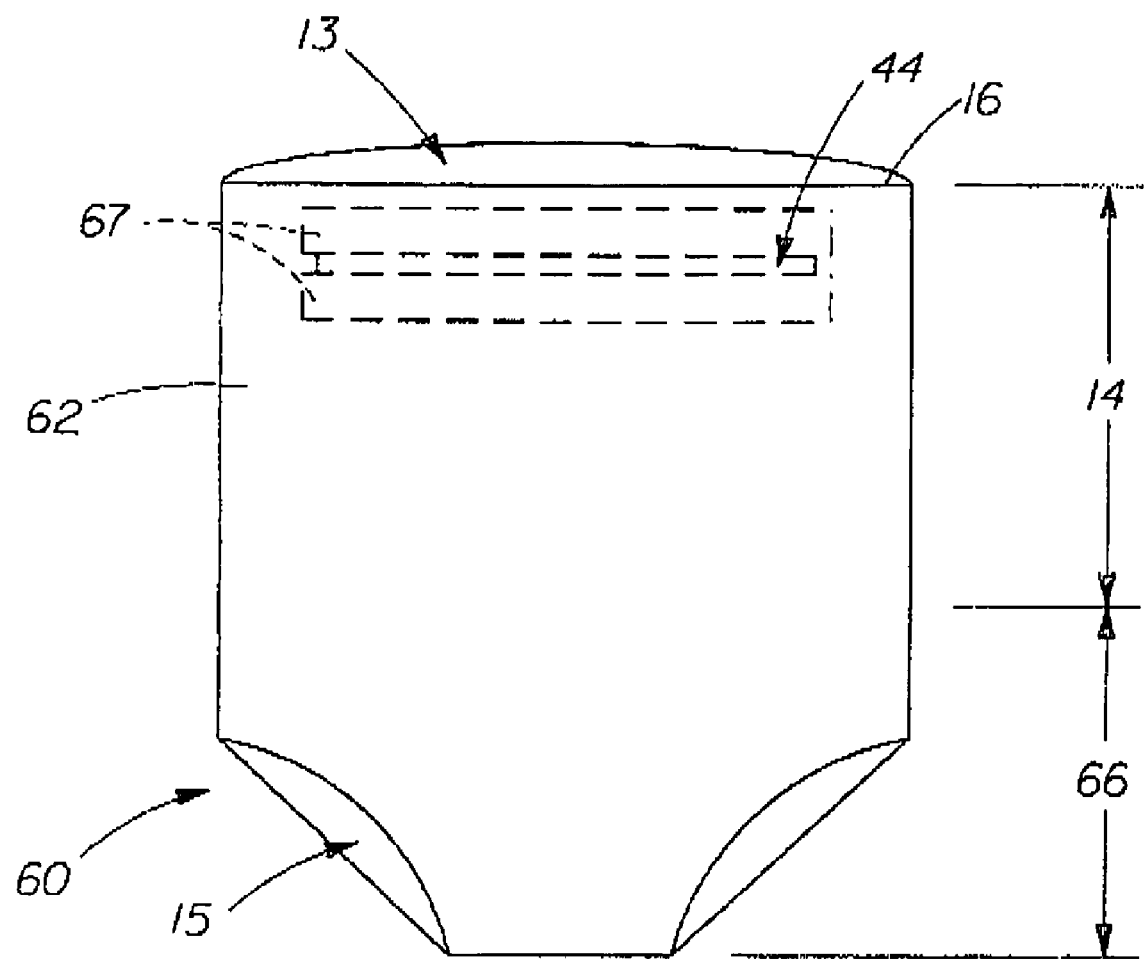
FIG. 14b illustrates a front view of a diaper having a chassis opening at the waist region in accordance with one embodiment.

Generally speaking, the diaper 60 includes a chassis forming a waist opening 13 and a pair of leg openings 15 (waist opening 13 and leg openings 15 shown in FIG. 14b). The diaper 60 has a longitudinal axis 17 and a lateral axis 18. The chassis has longitudinally opposed waist end edges 16a and 16b, back and front waist end edges respectively, longitudinally opposed waist regions 12 and 14, front waist region and back waist region respectively, a crotch region 66 longitudinally intermediate of the waist regions 12, 14, and laterally opposed side edges 64a and 64b, left side and right side respectively. The diaper 60 may also comprise first and/or first and second absorbent core components 52 and 51 (see FIGS. 2-4) disposed in the crotch region 66, and a replaceable absorbent core component 20 and/or 30 (see FIGS. 2-4) disposed in liquid communication, for example capillary liquid communication, with the absorbent core component. Elastic members 67a, 67b may be disposed in either or both of the waist regions 12 and 14 of the diaper 60 to provide a waistband. Elastic members 69a, 69b, 69c, 69d may be disposed intermediate the waist regions generally along the longitudinally extending laterally opposed side edges 64a and 64b to for elasticated leg cuffs. Fastening means, such as tape tab fasteners 65a, 65b, may be disposed in the waistband region of the diaper 60 for holding the diaper in position on the wearer. Generally, the placement of any of the elements of the diaper may be varied as suitable for the intended use. Thus, for example, the fastening means may be disposed at either waist region and are shown in the back waist region 14 in FIG. 1a and the front waist region 12 in FIG. 1b.

As will be described more fully, at least one access opening 44 may be provided for placement of a removable core component. FIG. 1b illustrates two such access openings 44, one being provided in each the waist regions 12, 14 of the diaper.

A barrier leg cuff 240 (see FIG. 1b) including a barrier leg cuff elastic member 241a/241b (see FIG. 1a) may be disposed adjacent to each longitudinal edge or between the longitudinal edge and the longitudinal axis 17 of the diaper. Suitable barrier leg cuff materials and structures are described in U.S. Pat. Nos. 4,695,278, 4,808,178, and 4,816,025, all of which are incorporated herein by reference.

Figure 4:
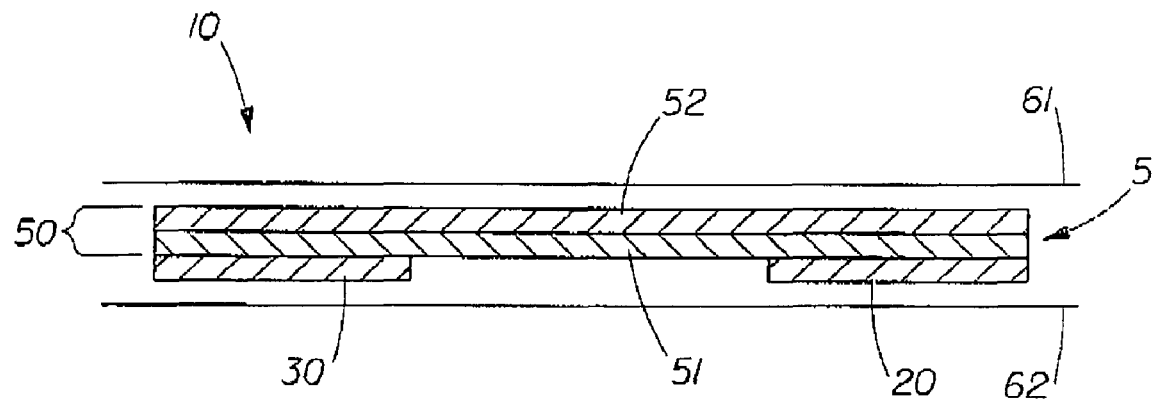
FIG. 4 illustrates a side cross sectional view of a replacement core against a topsheet in accordance with one embodiment.
Figure 3:
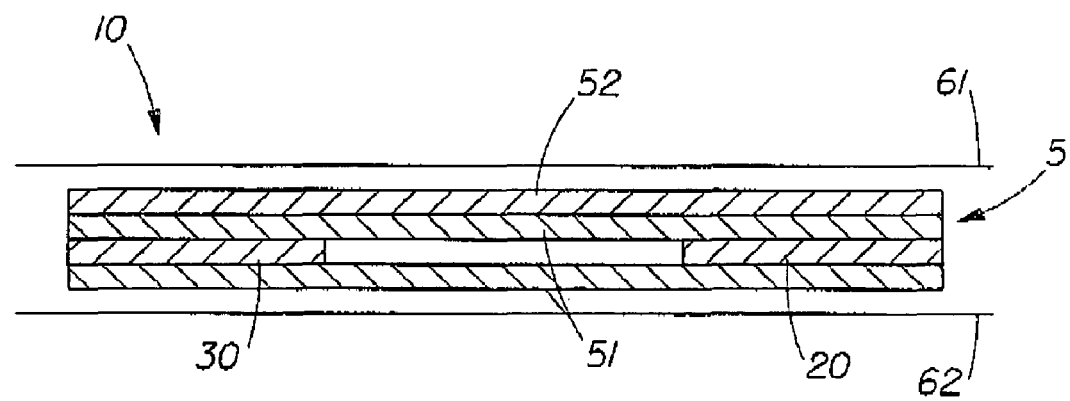
FIG. 3 illustrates a side cross sectional view of a replacement core between a backsheet and a topsheet in accordance with one embodiment.
Figure 2:
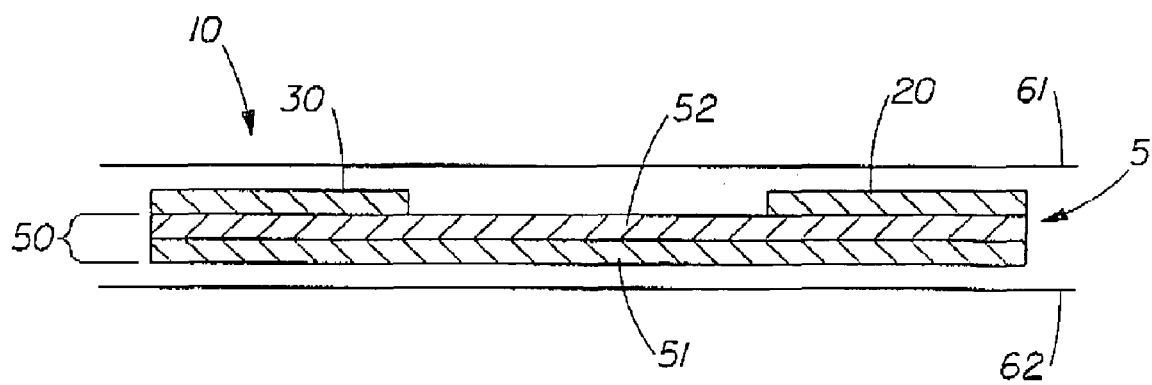
FIG. 2 illustrates a side cross sectional view of a replacement core against a backsheet in accordance with one embodiment.

FIGS. 2, 3 and 4 illustrate side views of layers of a diaper in accordance with various embodiments. In this disclosure, all description of replaceable absorbent core components, their removal and replacement, position within the chassis or openable chassis pocket and access to them for their removal and replacement, is generally applicable to any of the replaceable absorbent core components described herein and may be applied to a replaceable core component inserted proximate the front of the absorbent article or inserted proximate the back of the absorbent article. The replaceable absorbent core component may be inserted into the absorbent article prior to the application of the absorbent article to the wearer or while the absorbent article is being worn. When the replaceable absorbent core component is removed, a replacement absorbent core component may be inserted in place of the removed absorbent core component. See U.S. Pat. Nos. 6,932,800 and 6,989,006, which are both hereby incorporated by reference.

The absorbent article may include a plurality of absorbent core components, including first and second absorbent core components or layers 52 and 51, respectively, in capillary liquid communication with a replaceable absorbent core component 20 or 30. Any of the core components may have suitable liquid acquisition, acquisition/distribution, and/or storage/redistribution characteristics. Each of the absorbent core components may include multiple absorbent layers. Upon saturation with bodily discharges, the replaceable absorbent core component 30 or components may be removed from the absorbent article. New, unsaturated replaceable absorbent core components 20 and/or 30 may then be positioned in place of the removed saturated replaceable absorbent core components 20 and/or 30.

Figure 7:
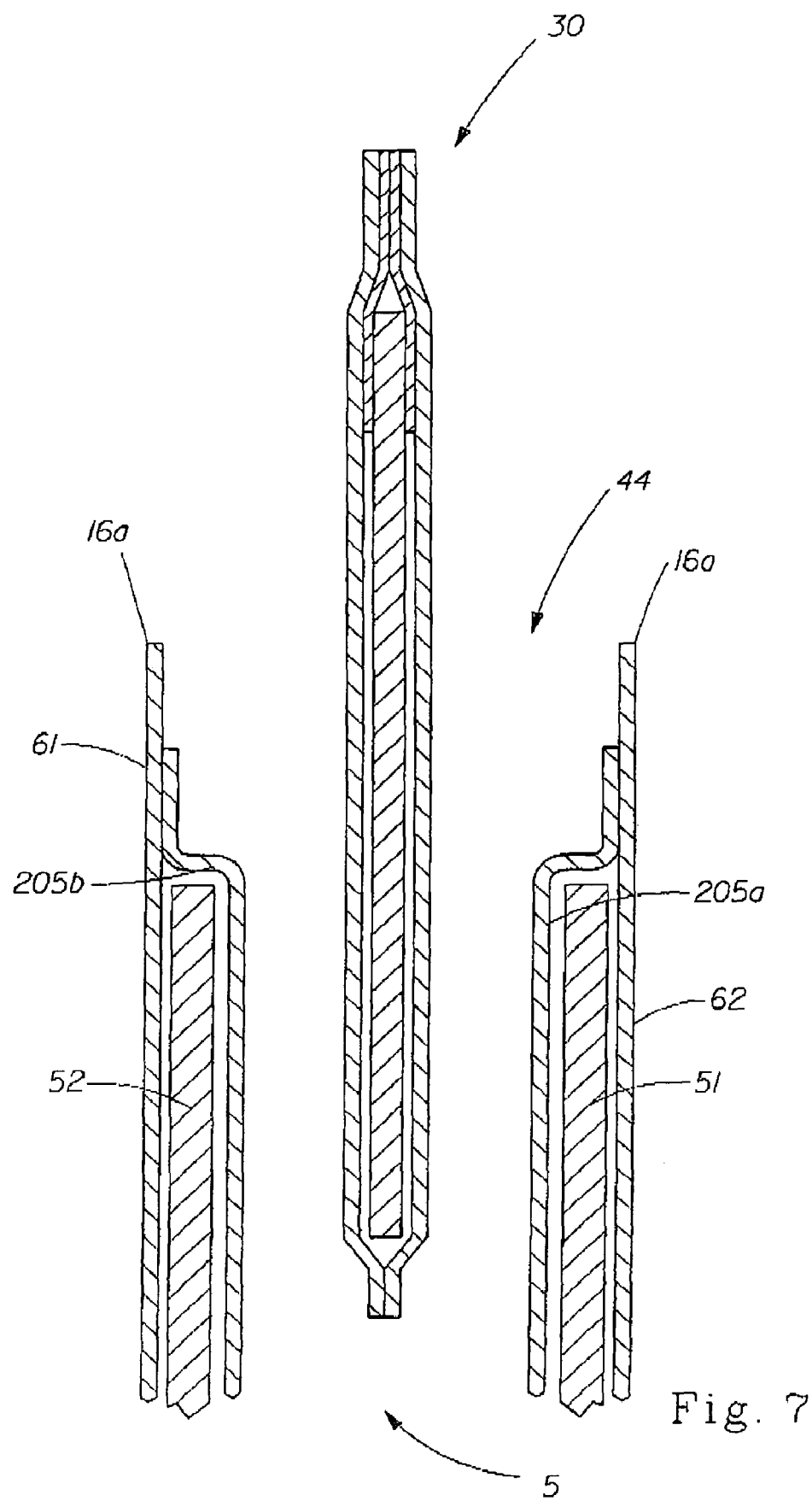
FIG. 7 illustrates a side cross sectional view of a diaper having an openable chassis pocket between two absorbent core components in accordance with one embodiment.
Figure 8:
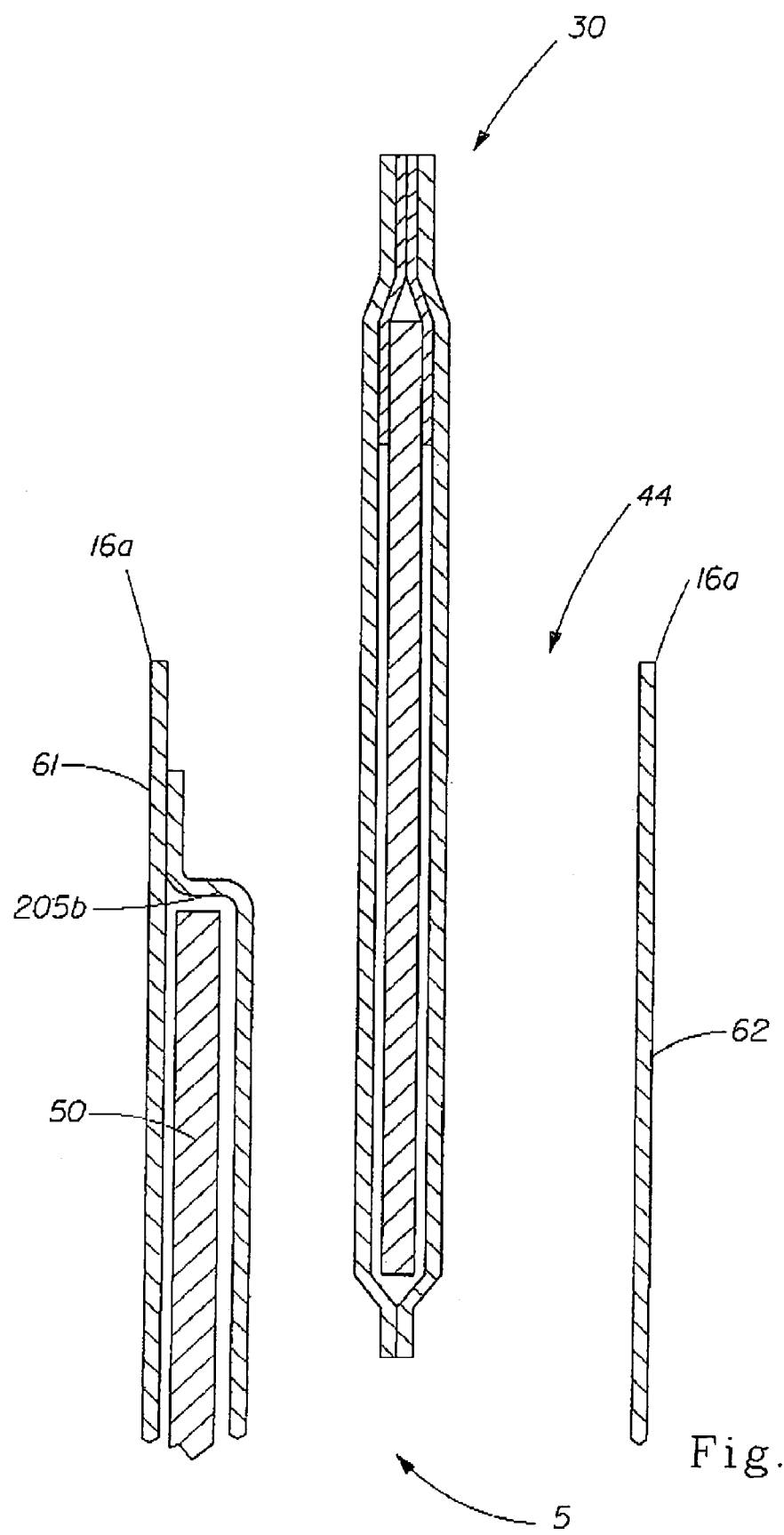
FIG. 8 illustrates a side cross sectional view of a diaper having an openable chassis pocket between an absorbent core and the backsheet in accordance with one embodiment.

As shown, the diaper comprises a topsheet 61, a first absorbent core component 52, a second absorbent core component 51, and a backsheet 62. In alternative embodiments the absorbent core component 50 may comprise a single layer of absorbent material instead of separate absorbent layers 51 and 52 as shown. The absorbent core 10 illustrated in FIGS. 2-4 comprise first and second core components 52 and 51, respectively, and at least one replaceable absorbent core component 20 and/or 30. It is understood that the absorbent core component 50 may comprise a single layer structure and may be a non removable absorbent core component. It should also be noted that only one or more replaceable core components may be disposed in the absorbent article. As will be described, an openable chassis pocket 5 for receipt of the replaceable absorbent core component, 20 or 30, may be disposed at various locations in the z-dimension of the diaper. The openable chassis pocket 5 may be formed between, for example, the absorbent core component 50 and the topsheet 61 as illustrated in FIGS. 2 and 6, between layers of the absorbent core component 50 as illustrated in FIGS. 3 and 7 or between the backsheet 62 and the absorbent core component 50 as illustrated in FIGS. 4 and 8.

Figure 5:
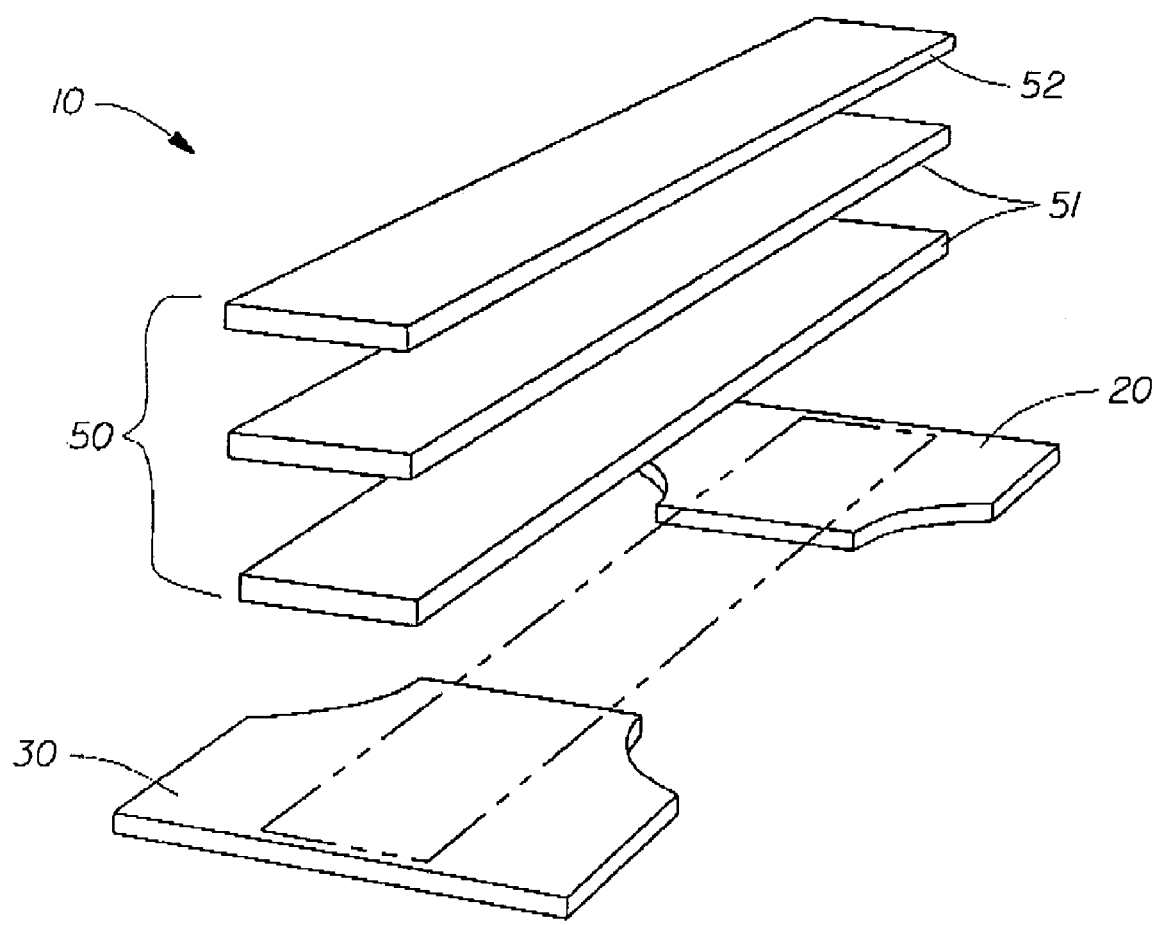
FIG. 5 illustrates an exploded view of an absorbent core in accordance with one embodiment.

FIG. 5 illustrates an exploded view of an absorbent core 10 in accordance with one embodiment. As shown, the absorbent core 10 may comprise two replaceable core components 30, 20 and an absorbent core component 50. The absorbent core component may comprise absorbent layers 51 and 52.

The replaceable absorbent core components 20 and/or 30 may be inserted into an openable chassis pocket 5 formed between layers of the diaper 60. The pocket 5 may be provided at any suitable location on the diaper 60, such as between or within any set of suitable layers. FIGS. 6-8 illustrates side cross sectional views of diapers having replaceable core components between differing layers of the diaper. Where not specifically discussed, reference is made to FIGS. 1a-4 for description of like element numbers.

Figure 6:
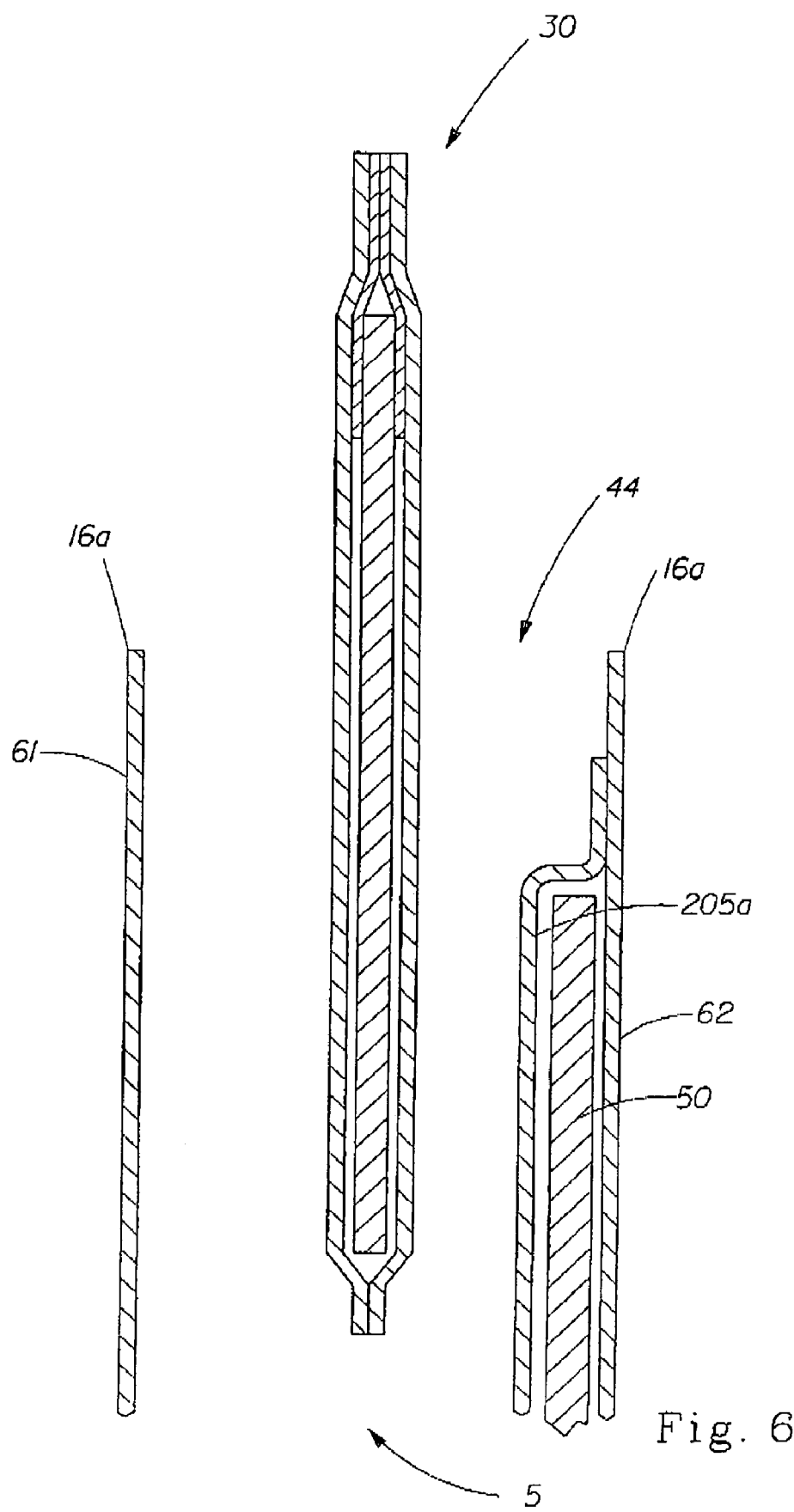
FIG. 6 illustrates a side cross sectional view of a diaper having a replaceable core component between the absorbent core and the topsheet in accordance with one embodiment.

As shown in FIG. 6, the replaceable core component 30 may be provided between the topsheet 61 and an absorbent core 50. The absorbent core 50 may be provided proximate the backsheet 62. A liquid pervious layer 205a may be provided associated with the absorbent core 50. As shown, the replaceable core component 30 is inserted in the openable chassis pocket 5 through the access opening 44.

As shown in FIG. 7, the replaceable core component 30 may be provided between absorbent layers 51 and 52, with one absorbent layer 51 being provided proximate the backsheet 62 and one absorbent layer 52 being provided proximate the topsheet 61. A liquid pervious layer 205a, 205b may be provided associated with each of the absorbent layers 51, 52. As shown, the replaceable core component 30 is inserted in the openable chassis pocket 5 through the access opening 44.

As shown in FIG. 8, the replaceable core component 30 may be provided between the backsheet 62 and an absorbent core 50. The absorbent core 50 may be provided proximate the backsheet 62. A liquid pervious layer 205a may be provided associated with the absorbent core 50. As shown, the replaceable core component 30 is inserted in the openable chassis pocket 5 through the access opening 44.

As discussed, a liquid pervious layer or sheet 205a or 205b may be provided. For example, the liquid pervious layer or sheet 205a or 206b may be a tissue sheet, or a scrim layer, and may be positioned within the core structure, such as between an acquisition/distribution component and a storage/redistribution component to maintain the physical integrity of the acquisition/distribution component during processing and/or use. This liquid pervious sheet 205a, 205b can envelop all or part of an acquisition/distribution component of the core 10, or simply be positioned as described above, without enveloping the acquisition/distribution component. The liquid pervious sheet 205a, 205b may also form all or part of the openable chassis pocket 5.

The layers of the diaper 60 may be joined together at least about a portion of the periphery 57 of the absorbent article. As discussed with respect to FIG. 1b, an access opening 44 may be provided for accessing the openable chassis pocket 5. In the embodiment of FIG. 1b, the access opening 44 comprises slots provided along the garment facing portion 3 of the diaper 50. In alternative embodiments, such as shown in FIGS. 6-8, in a predetermined area of the periphery 57, the wearer facing portion 2 of the diaper 60, comprising at least a topsheet 61, and the garment facing portion 3, comprising at least an impermeable backsheet 62, may remain non-joined to form an opening 44 along the periphery providing access to the openable chassis pocket 5 for receipt of the replaceable absorbent core component 20, 30.

Referring again to FIGS. 1a and 1b, the topsheet 61 may be liquid pervious permitting liquids (e.g., urine) to penetrate there through. Generally, the topsheet 61 may be compliant, soft feeling, and non-irritating to the wearer's skin. A suitable topsheet 61 can be manufactured from a wide range of materials such as woven and nonwoven materials; polymeric materials such as apertured formed thermoplastic films, apertured plastic films, and hydro-formed thermoplastic films; porous foams; reticulated foams; reticulated thermoplastic films; and thermoplastic scrims. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. In one embodiment, the topsheet 61 is made of a hydrophobic material to isolate the wearer's skin from liquids contained in the absorbent core 10 that is treated on at least one side with a surfactant to allow liquids to readily penetrate there through. The topsheet 61 may comprise one or more layers.

High loft nonwoven topsheets and apertured formed film topsheets may be used. Apertured formed films are pervious to bodily liquids, non-absorbent, and have a reduced tendency to allow liquids to pass through in a direction away from the absorbent core 10 and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet 61 rather than flowing into and being absorbed by the absorbent core 10.

The topsheet 61 is positioned above the wearer facing surface of the absorbent core 10. The topsheet 61 may be formed by a single layer or more than one layer. An acquisition material may be positioned between absorbent core 10 and topsheet 61. As will be described below, in embodiments wherein the wearer facing portion 2 comprises at least one absorbent core component, the composite includes the topsheet 61 and may include a second fluid pervious layer 205a or 205b (see FIGS. 6-8) with at least a portion of the absorbent core component 50 being disposed between the topsheet 61 and the second fluid pervious layer 205a or 205b.

The backsheet 62 may be impervious to liquids (e.g., urine), and yet may permit vapors to escape from the absorbent core 10 (i.e., breathable). The backsheet 62 may prevent the exudates absorbed and contained in the absorbent core from wetting articles that contact the diaper 60, such as bed sheets and undergarments. The backsheet 62 may comprise any suitable material, including a woven or nonwoven material, polymeric films such as thermoplastic films of polyethylene or polypropylene, composite materials such as a film-coated nonwoven material, other materials, or combinations of thereof. In the embodiments discussed, the backsheet 62 may comprise a liquid impermeable layer and a vapor permeable layer. The impermeable layer may comprise a poly material and the permeable layer may comprise a carrier nonwoven web. The impermeable layer may comprise a thermoplastic film having a thickness of from about 0.012 mm (0.5 mils) to about 0.051 mm (2.0 mils), although other flexible liquid impervious materials can be used. As used herein, the term "flexible" refers to materials that are compliant and that readily conform to the general shape and contour of the wearer's body. Suitable polymeric films for use as the impermeable layer may contain a high content of linear low density polyethylene. In some embodiments, the impermeable layer may include blends comprising about 45-90% linear low density polyethylene and about 10-55% polypropylene, or any other suitable quantities. Exemplary films for use as the impermeable layer are manufactured by Tredegar Industries, Inc. of Terre Haute, Ind. under the designations X-8323, RR8220 blend for certain blown films, and RR5475 blend for certain cast films, and are manufactured by Monsanto Chemical Corporation and marketed in the trade as Film No. 8020. The backsheet 62 may be embossed and/or matte finished providing a more cloth-like appearance. In embodiments wherein the garment facing portion comprises at least one absorbent core component, the composite may include a liquid pervious layer 205a or 205b (see FIGS. 6-8), a backsheet 62 for example a substantially liquid impervious layer, and a nonwoven cover layer. At least a portion of absorbent core component 50 may be disposed between the backsheet 62 and the liquid pervious layer 205a or 205b.

In some embodiments, the topsheet 61 and the backsheet 62 are coextensive and have length and width dimensions generally larger than those of the absorbent core 10. Alternatively, the topsheet 61 may be slightly smaller than the backsheet 62. Generally, the size of the backsheet 62 and/or topsheet 61 is dictated by the size of the absorbent core 10 and the absorbent article design selected.

The absorbent core 10 is provided between the topsheet 61 and the backsheet 62. As previously discussed, in some embodiments, the absorbent core comprises first and second absorbent core components or layers 52 and 51 and a replaceable absorbent core component 20 or 30. The dimensions, for example, the length and extension, of the first and second absorbent core components 52 and 51, respectively, and the replaceable absorbent core component 20 or 30 may be varied to suit the design of the particular absorbent article. In the case of diapers, the replaceable absorbent core component 20 and/or 30 can extend from one or both of the front or back waist regions 12 or 14 respectively into the crotch region 66 of the diaper. The absorbent core components or layers 51, 52 can extend from one of the waist regions 12 or 14 through the crotch region 66 into the opposing waist region. The absorbent core components or layers 51, 52 may not be coextensive. The front and back waist regions 12 and 14 respectively can be determined by measuring from the front waist end edge of the absorbent article or back waist end edge of the absorbent article, respectively, 25% of the total length of the absorbent article. The crotch region 66 is the region between the front and back waist regions which represents the remaining 50% of the total length of the diaper 60. In alternative embodiments, the percentage length of the diaper attributed to each of the front waist region, back waist region, and crotch region may be varied.

The absorbent core 10 and components thereof may comprise any absorbent material capable of absorbing and retaining liquids such as urine and other body exudates. The absorbent core 10 can be of any suitable shape. For example, the absorbent core 10 may be provided in an hour glass configuration, wherein the core has generally arcuate cutouts in its longitudinal edges, or in a generally rectilinear configuration. The shape and configuration of each component of the core may be varied. Generally, the absorbent core components may be substantially rectilinear, may have increasing width at leading and trailing edges thereof, or may have varying widths along their length. The absorbent core component 50 may be disposed such that they are generally non-removable from the diaper chassis. The replaceable absorbent core component 20 and/or 30 is shaped for receipt by the pocket and may be generally rectilinear, or any other suitable shape, such as a trapezoid, wedge, triangle, etc. The term "generally rectilinear" refers to a center section having a generally constant width along its length. At least one of the absorbent core components or layers, 52, 51, is typically in liquid communication, for example capillary liquid communication, with the replaceable absorbent core component 20 or 30, as received by the pocket 5, but need not be coextensive therewith.

A multi-piece absorbent core 10 having discrete components may provide benefits. First, the core may exhibit desirable aesthetics and fit when used in an absorbent article, due to the use of discontinuous absorbent layers or panels of absorbent material. For example, the center section of the core may include separate absorbent layers allowing the center section to bend and buckle somewhat independently and thereby provide improved fit and comfort in the crotch area.

Another potential advantage provided by a multi-piece absorbent core 10 is the ability to independently vary selected characteristics of the absorbent core components and members. The characteristics that may be varied include the acquisition rates, distribution rates, storage capacities and rates, interfacial liquid transfer rates and efficiencies, thickness, functionality, shape or configuration of the absorbent layers or panels, etc. For example, an absorbent layer closest to the body of the wearer may have relatively greater acquisition characteristics than two outer absorbent layers having relatively greater acquisition/distribution characteristics. In this configuration, bodily discharges such as urine are quickly acquired by the acquisition/distribution member and/or a storage/redistribution member.

A third potential benefit resulting from the use of a multi-piece absorbent core 10 is the capability of removing and/or replacing components of the absorbent core to regenerate the storage/redistribution capacity of the absorbent core. The provision of access to the replaceable absorbent core component 30 allows the removal and/or replacement of that absorbent core component.

By replacing absorbent core components, particularly absorbent core components that are primarily suited for storage/redistribution, the use of the absorbent article, such as the disposable diaper, may be prolonged while continuing to draw moisture away from the wearer's skin. As core members become saturated, they may become substantially less effective at absorbing moisture. As an absorbent core component becomes more saturated, its ability to absorb as much moisture away from the wearer's skin is hindered. Once a replaceable absorbent core component 20 or 30 is replaced, the absorption of the absorbent core component 50 in the chassis is renewed or regenerated, and it once again becomes capable of absorbing moisture. Therefore, the absorbent article may be worn longer, and regeneration of the absorbent core may be made without removal of the article from the wearer.

Any of the core components may include multiple layers of absorbent material, each having individual liquid acquisition, acquisition/distribution, or storage/redistribution characteristics, as well as individual shape, width, length, and thickness characteristics. The number and placement of absorbent layers may be varied to achieve desired characteristics such as thinness, softness, flexibility, or beneficial liquid acquisition, distribution, and storage rates, as well as capacity and storage rates, wearer comfort, etc. The components or members of the absorbent core may include laminates or combinations of several sheets or webs of materials. In general, each absorbent core component or member may be made of any absorbent material or combination of materials having enough structural integrity to be handled as a discrete unit.

Any suitable material or materials may be used for the absorbent core components. For example, suitable materials include fibrous nonwoven materials, fibrous air-laid materials, fibrous wet-laid web materials, and combinations of fibrous materials having absorbent gelling materials dispersed upon or within the fibrous structure. Such absorbent core components may be formed into an insert packet having the fibrous materials substantially enveloped by a liquid pervious web that provides the structural integrity for the removal and replacement into the absorbent article. An exemplary form of a non-woven fibrous absorbent structure that may be utilized is constructed from hydrophilic chemically stiffened cellulosic fibers. Absorbent materials for use as absorbent core components or members may also be foam-based. For example, a component of the absorbent core may include a foam material in the form of a sheet or a plurality of foam pieces or particles, which may be adhesively bonded together or which may simply be constrained into an unbonded aggregate held together by an overwrapping of envelope tissue or by means of the topsheet 61 and backsheet 62 of the absorbent article. Suitable absorbent foams for absorbent articles such as diapers have been made from High Internal Phase Emulsions, hereafter referred to as "HIPE." The absorbent core 10 of the absorbent articles described herein also can include a combination of materials, such as a combination of conventional elements or materials and one or more foam absorbent structures. For example, the absorbent articles may utilize an absorbent core that includes a combination, e.g., an airlaid mixture, of particles or pieces of the foam absorbent structures and conventional absorbent materials such as wood pulp or other cellulosic fibers and/or particles or fibers of polymeric gelling agents.

The absorbent core 10 may comprise acquisition components, acquisition and transfer components, storage and redistribution components, or any other suitable components. The acquisition component generally is the uppermost absorbent layer or core component and acquires the fluid and distributes the fluid away from the wearer's body to the generally more absorptive core components provided beneath the uppermost absorbent layer. Thus, the uppermost absorbent layer is generally on the side corresponding to the body side of an absorbent article, and is generally in capillary liquid communication with the topsheet 61 of the disposable diaper, thereby acting to quickly acquire and partition bodily exudates. An acquisition and transfer component acquires the fluid and transfers it to another component. An acquisition and storage acquires and holds the fluid and may redistribute the fluid within the component. The function of each of the chassis absorbent core components or layers, 52 and 51, and replaceable components, 20 or 30, may depend on the positioning of the openable chassis pocket 5 within the layers of the diaper, as described more fully with respect to the method of manufacturing the diaper.

Besides acquiring bodily liquids rapidly, an absorbent acquisition component may transfer liquid efficiently to liquid acquisition/distribution or storage/redistribution components. This liquid transfer function of the acquisition member may involve the acquisition member having sufficient capillary suction to substantially drain the liquid from the topsheet 61 and yet not exhibit excessive liquid retention, which would make it difficult for an underlying absorbent layer to desorb the acquisition component. In particular, the liquid acquisition component generally may have a suitable capillary desorption pressure relative to the absorption pressure of other absorbent core components, especially those intended for liquid storage. If the liquid acquisition component of the absorbent article holds the acquired liquid, this may inhibit the ability of these other components to partition liquid away, and can cause the acquisition component to remain loaded with liquid such that the absorbent article is more susceptible to leaking.

The liquid acquisition/distribution component generally has more distributive characteristics than the acquisition component. Since discharged aqueous bodily liquid, e.g., urine, is frequently discharged in gushes, the acquisition/distribution component may acquires this liquid and transport the liquid by wicking or another mechanism from the point of initial liquid loading to other parts of the acquisition/distribution component for eventual desorption to the adjacent liquid storage/redistribution component. Thus, such materials may have a greater degree of distributive capacity than the acquisition component materials, such that bodily exudates may be efficiently transported from the acquisition zone to the storage component of the absorbent core.

A suitable absorbent core includes a liquid storage/redistribution component. The liquid storage/redistribution component may act to store bodily exudates away from the wearer's body, so as to leave the wearer with a feeling of dryness and to prevent leakage. The storage/redistribution component may be maintained in capillary liquid communication with the acquisition and/or acquisition/distribution component(s), such that urine or other aqueous bodily liquids can be desorbed from the acquisition and/or acquisition/distribution component(s) and be absorbed by the liquid storage/redistribution component.

The storage/redistribution component may include a member or members having primarily liquid storage characteristics. Such a storage member may have limited transport and wicking capabilities but high storage or retention capacity, and rely upon a liquid distribution member to distribute incoming liquid over a larger area of the storage/redistribution member.

In some embodiments, it may be desirable to have a "biased" absorbent core structure, wherein a portion adjacent to one surface is capable of rapidly acquiring a liquid with reduced dispersion, while a portion adjacent to an opposing surface is capable of rapidly dispersing a liquid with lesser acquisition capability. When oriented in an absorbent article such that the "acquisition side" is oriented toward the wearer and the "distribution side" is oriented away from the wearer, a "down and out" functionality is provided, whereby liquid may be rapidly acquired into the absorbent core structure with reduced dispersion on its wearer-facing side and rapidly distributed throughout the portion of the absorbent core structure on its garment-facing side. This functionality allows the maintenance of a clean and dry visible and tactile impression of the absorbent core structure, and hence the absorbent article, while effectively utilizing the absorptive capacity of the regions of the absorbent article oriented away from the wearer.

To provide the above-described functionality, compositions for the absorbent core 10 may be selected such that the acquisition side of the absorbent layer is comparatively free of small, high surface area fibers that provide good distributive and storage characteristics, and such that the distributive side of the absorbent layer has a comparatively higher proportion of such small, high surface area fibers so as to provide greater distribution characteristics. In some embodiments, the acquisition area may have both a relatively lower average density and lower average basis weight per unit area than the distribution area to establish a capillarity force gradient between them. Also, in foam absorbent core structures, cell sizes and hole sizes are parameters that can impact a number of important mechanical and performance features of the foams, including their fluid wicking properties and the capillary pressure that is developed within the foam structure.

FIGS. 9-13 illustrate replaceable absorbent core components being inserted or in place within an openable chassis pocket. Where not specifically discussed, reference is made to FIGS. 1a-8 for description of like element numbers.

Figure 9:
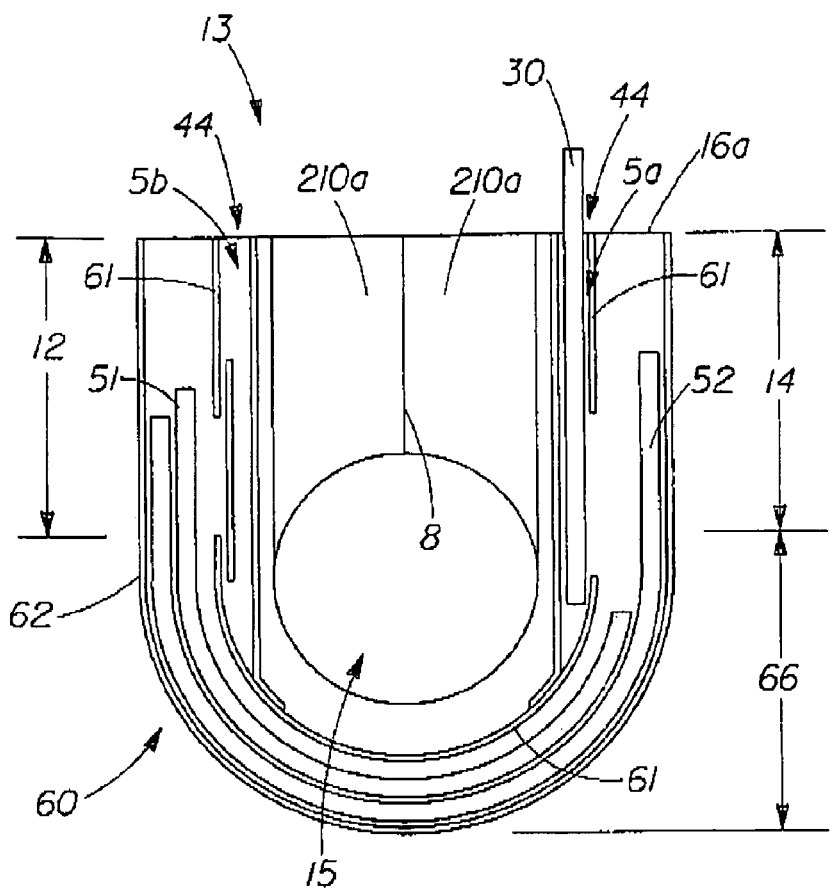
FIG. 9 is a side cross sectional view of a diaper in a closed configuration with a replaceable absorbent core being inserted in an openable chassis pocket in accordance with one embodiment.
Figure 10:
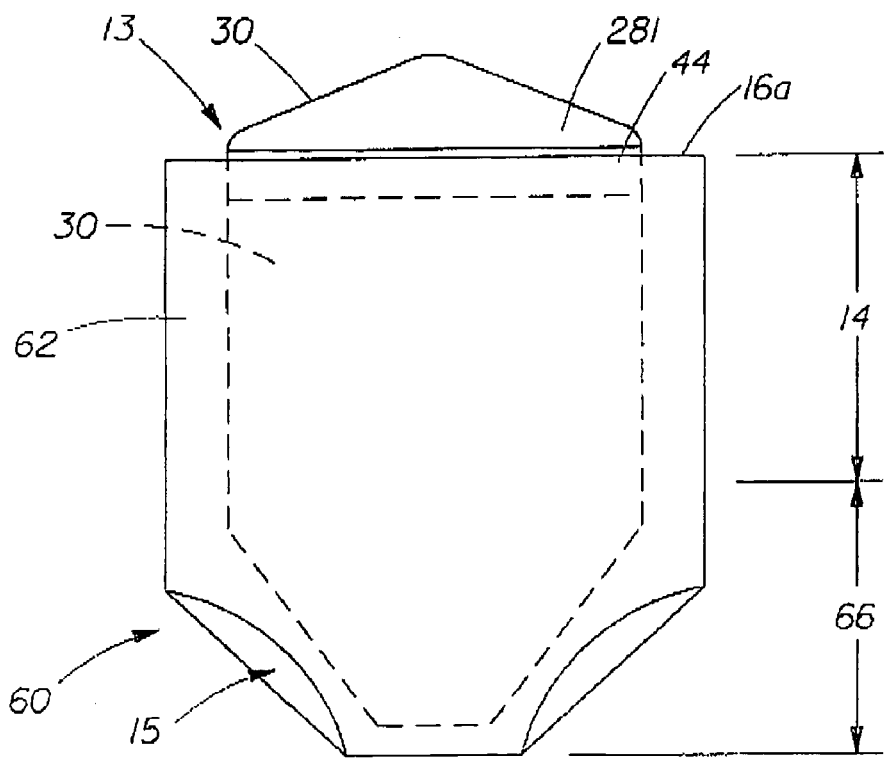
FIG. 10 illustrates a front view of a diaper with a replaceable core component positioned at the waist edge in accordance with one embodiment.
Figure 11:
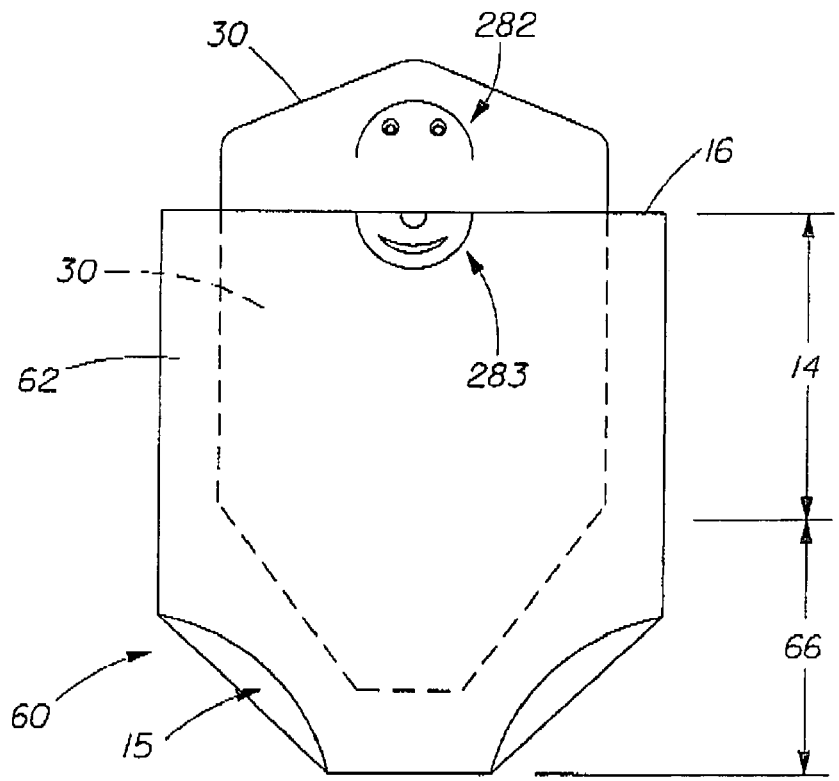
FIG. 11 illustrates a front view of a diaper with a replaceable core component and positioning indicia wherein the replaceable core component is not positioned in accordance with one embodiment.
Figure 12:
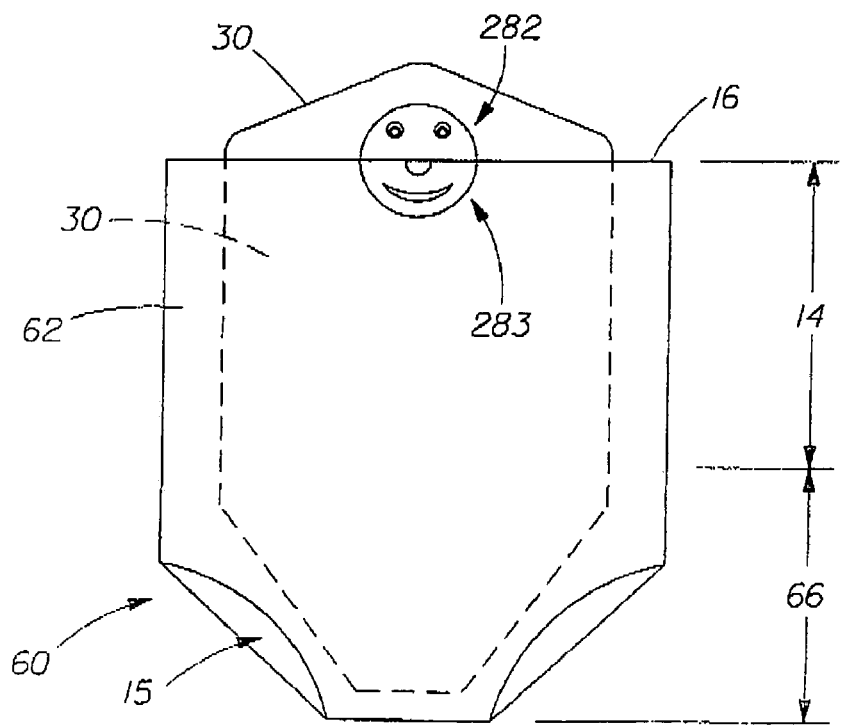
FIG. 12 illustrates a front view of a diaper with a replaceable core component and positioning indicia wherein the replaceable core component is positioned in accordance with one embodiment.

As shown in FIG. 9, the replaceable absorbent core component 30 is inserted into an openable chassis pocket 5a through an access opening 44. In the embodiment shown, the access opening 44 is shown at the back waist region 14 at the waist opening 13. A second openable chassis pocket 5b may be provided at the front waist region 12. The first absorbent core component or layer 52 is shown beginning along the back waist region 14 and the second absorbent core component or layer 51 is shown beginning along the front waist region 12. In the embodiment shown, the first and second absorbent core components or layers 52, 51 are partially coextensive. FIG. 9 further illustrates elastic side panels 210a extending generally from the waist opening 13 to the leg opening 15. Regardless of the specific characteristics of the replaceable absorbent core component 20 and/or 30, the replaceable absorbent core component and/or the absorbent article may comprise indicators for indicating proper positioning of the replaceable absorbent core component within the article. FIGS. 10-12 illustrate various embodiments of a diaper with a replaceable core component and positioning indicia for indicating correct positioning of the replaceable core component in an openable chassis pocket.

FIG. 10 illustrates a front view of a replaceable absorbent core component 30 being inserted into an access opening 44 along the waist opening 13. In the embodiment of FIG. 10, the indicator comprises a visible indicator line 281 positioned in the outer end segment of the replaceable core component 30 such that the line is aligned with the waist end edge 16a of the chassis when the predetermined position of the replaceable core component is reached.

FIGS. 11 and 12 illustrate an alternative embodiment of a visible indicator. As shown, the indicator may comprise a graphical object 282 on the replaceable core component 30 may align with a complementary graphical object 283 on the chassis to form a side-by-side composite graphical object when a predetermined position of the replaceable core component is reached. The replaceable absorbent core component 30 may simply include a half circle indicator 282 and the absorbent article 60 may include a complementary half circle indicator 283, such that, when proper positioning has been achieved, the two half circle indicators generally form a circle. It is to be recognized that the indicators may be any suitable shape, whether or not complementary.

Figure 13:
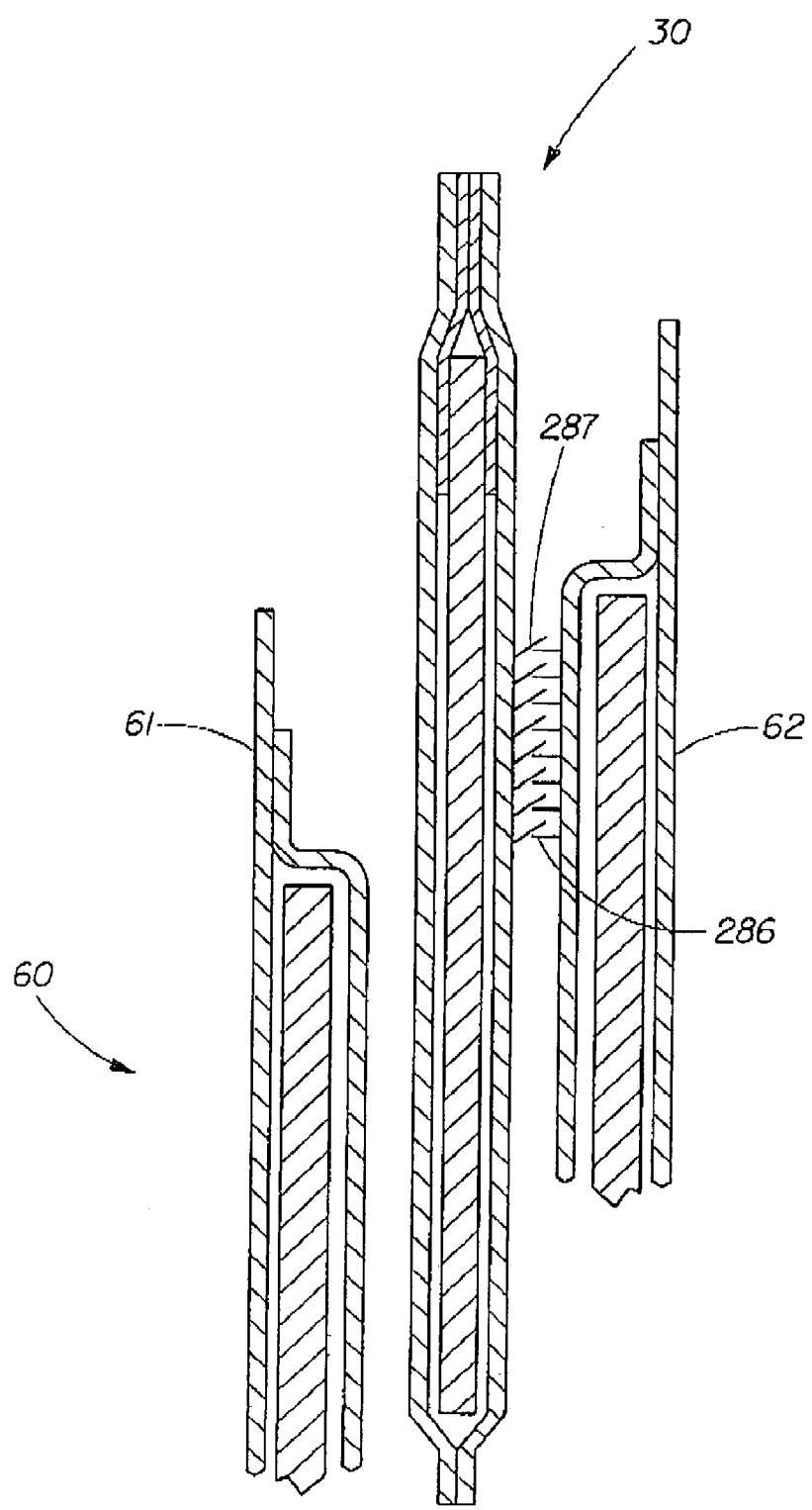
FIG. 13 illustrates a side cross sectional view of a diaper having a replaceable core component with a fastening element in accordance with one embodiment.

Fastening members also may be included for fastening the replaceable absorbent core component 30 in place as shown in FIG. 13. FIG. 13 illustrates the replaceable absorbent core component 30 inserted in the openable chassis pocket 5 between the topsheet 61 and the backsheet 62. In the embodiment shown, the fastening member comprises a hook-and-loop fastener. However, other fastening members may be used. The hook-and-loop fastener includes one member (e.g., the hooks) 287 on the replaceable absorbent core component 30 and the other member (e.g., the loops) 286 within the operable chassis pocket 5 of the absorbent article 60. Thus, for example, one member of a hook-and-loop fastener 287 may be provided below the half circle indicator of the replaceable absorbent core component 30 and the other member of the hook-and-loop fastener 286 may be provided behind the half circle of the absorbent article. Thus, when properly positioned, the two half circle indicators align and/or the hook-and-loop fastener engages. Any other suitable fastening mechanism also may be used and/or any type of indicators for receiving portions of the fastening mechanism may be used.

In summary, the absorbent core 10 may include a plurality of discrete components, each component having distinct liquid acquisition, acquisition/distribution, or storage/redistribution characteristics. So long as each of the acquisition, acquisition/distribution, and storage/redistribution components is in communication with an adjacent component or components, the absorbent core components may be positioned relative to one another in a wide variety of configurations. Any suitable positional relationship of an acquisition component, an acquisition/distribution component, and a storage/redistribution component within the absorbent core may be used. These components may be in effective liquid communication with each other, with each component being capable of effectively holding and/or transporting the amount of aqueous bodily liquid that is expected to be discharged into the absorbent article. Further, an absorbent core may not include each of a liquid acquisition component, an acquisition/distribution component, and a storage/redistribution component, or may include more than one of any component.

The diaper 60 may further comprise elastic members that exert a contracting force on the diaper so that it configures more closely and more comfortably to the wearer. Elastic members can be assembled in a variety of well known configurations, such as those described generally in U.S. Pat. No. 3,860,003. Leg elastic members may be disposed adjacent to the periphery of the diaper, such as along each longitudinal edge to form an elastically contractible leg cuff. FIG. 1a illustrates leg elastic members 69a-69d. The elastic members 69a-69d tend to draw and hold the diaper 60 against the legs of the wearer. The leg elastic members 69a-69d may extend along a portion of the length of the diaper. Alternatively, the leg elastic members 69a-69d may generally extend the length of the diaper, or any other length suitable to provide an elastically contractible line. The length of the leg elastic members is guided by the diaper design. A barrier leg cuff 240 (see FIG. 1b) including a barrier leg cuff elastic member 241a/241b (see FIG. 1a) may be disposed adjacent to each longitudinal edge or between the longitudinal edge and the longitudinal axis 17 of the diaper. Suitable barrier leg cuff materials and structures are described in U.S. Pat. Nos. 4,695,278, 4,808, 178, and 4,816,025, all of which are incorporated herein by reference.

Again referring to FIGS. 1a and 1b, elastic members can be disposed in either or both of the waist regions 12 and 14 of diaper 60 to provide a waistband 67a, 67b as well as disposed adjacent the waist regions to form leg cuffs. See, for example, U.S. Pat. No. 4,515,595. The elastic members may be secured to the diaper 60 in an elastically contractible condition so that, in a normally unrestrained configuration, these elastic members effectively contract or gather the diaper. The elastic members can extend generally the length of the diaper 60 in the crotch region 66, the length of the diaper 60, or any other length suitable to provide an elastically contractible line. The length of these elastic members may be guided by the diaper's design. While the waistband 67a, 67b can comprise a separate element affixed to the body of the disposable diaper 60, it alternatively may comprise an extension of other elements of the disposable diaper, such as the backsheet 62 or the topsheet 61 or both the backsheet and the topsheet. In one exemplary embodiment illustrated in the '595 patent, elastic waist elements extend across generally the lateral width of the disposable diaper. Similar waistbands may be useful in designs wherein the elastic waist elements extend across only a portion of the lateral width of the diaper. In one embodiment, the elastic waist elements extend across a major portion of the lateral width of the disposable diaper.

The absorbent article may have an "open" chassis configuration, as shown in FIGS. 1a and 1b, in which the chassis is adapted to be fastened together about the lower torso of a wearer by the fastening means. Alternatively, the absorbent article may have a "closed" chassis configuration, such as that of a pull-on pant-type diaper or training pant, in which the chassis is adapted to be pulled on over the legs and lower torso of the wearer without any additional fastening steps. Fastening means, such as tape tab fasteners 65 may be disposed in the waist region of the diaper 60 for holding the diaper on the wearer.

Returning to FIG. 9, a diaper 60 in a closed configuration with the replaceable absorbent core component 30 in place is shown. In the embodiment of FIG. 9, the diaper 60 has a closed chassis configuration and is adapted to be pulled on. As shown, a access opening 44 is provided along the waist edge 16 to an openable chassis pocket 5a, with a replaceable absorbent core component 30 being disposed inside the openable chassis pocket 5a and with an openable chassis pocket 5b being provided for receiving a second replaceable absorbent core component. The replaceable absorbent core component 30 is removable from and replaceable into the openable chassis pocket 5a through the access opening 44. For example, after the removal of a saturated replaceable absorbent core component, a fresh, unused absorbent core component may be inserted through the openable end 41a. In the embodiment of FIG. 9, a first openable chassis pocket 5b is provided in the front waist region 12 and a second openable chassis pocket 5a is provided in the back waist region 14. This in this embodiment, the diaper 60 comprises two openable chassis pockets, 5a and 5b, adapted for receiving replaceable absorbent core components, 20 or 30, however, as few as one replaceable absorbent core component may be disposed within the openable chassis pockets and only one openable chassis pocket may be provided.

FIGS. 14a and 14b illustrate alternative embodiments of access openings. Where not specifically discussed, reference is made to FIGS. 1a-13 for description of like element numbers. As shown in FIG. 14a, the access opening 44 of the openable chassis pocket 5 may be formed along a predetermined area of the periphery 57, such as along a waist end edge 16, either in the front, in the back, or both, where the wearer facing portion and the garment facing portion are separable to provide access to the replaceable absorbent core component 30. The access opening 44 is formed by the separation of the wearer facing portion 2 and the garment facing portion 3 and allows the removal and replacement of the replaceable absorbent core component 30 and may be resealable to provide a substantial degree of liquid impermeability when closed. A closing mechanism 43, such as a hook-and-loop fastener, may thus be provided. In the embodiment shown, one member of the closing mechanism is provided on the backsheet 62 and a complementary member of the closing mechanism is provided on the topsheet 51.

Alternatively, as shown in FIG. 14b, the access opening 44 of the openable chassis pocket 5 may be formed in a waist region, either in the front waist region 12, in the back waist region 14, or both, where the wearer facing portion or the garment facing portion comprises an opening 44 to provide access to the openable chassis pocket 5. In the embodiment shown, the access opening 44 is formed on the wearer facing portion 2, through the backsheet 62, along the back waist region 14. The access opening 44 allows the removal and replacement of the replaceable absorbent core component. FIG. 14b further illustrates elastic waistband members 67 proximate the access opening 44. The elastic waistband 67 may be disposed in the waist region between the end edge and an adjacent end of the absorbent core.

Referring to the embodiment of FIG. 1a, when an elastic waistband 67a, 67b is disposed adjacent to an access opening 44 formed by the separation of the wearer facing portion 2 and the garment facing portion 3 along a waist end edge 16, the waistband 67a, 67b may serve to make the opening 44 elastically openable and self-closing. For example, such an elastic waistband 67a, 67b, formed as a separate element affixed to the backsheet 62 or as an extension of the backsheet 62 in the waist region, may exert a contractive force, tending to draw the waist end edge 16 of the backsheet 62 at the periphery toward the topsheet 61, thus tending to close the access opening 44 of the openable chassis pocket 5 when it is released.

Alternatively, or additionally, a contact portion may be provided adjacent the access opening 44. The contact portion may be used to maintain the topsheet 61 in contact with the wearer when the access opening 44 is opened. In one embodiment, the contact portion comprises a band extending generally from one lateral side of the diaper 60 to another lateral side of the diaper 60 along the topsheet 61 adjacent the access opening 44. The band may be integral with the topsheet 61 or may be separate from and coupled to the topsheet. The band exerts a contractive force on the topsheet 61 to hold the waist edge of topsheet 61 against the wearer when the garment facing portion of the diaper 60 is pulled to open the access opening 44. Any suitable contact portion may be used. As another example, an elastic waistband 67, formed as either a separate element affixed to the topsheet 61 or as an extension of the topsheet 61 in the waist region, may exert a contractive force tending to hold the waist end edge 16 of the topsheet 61 against the body of the wearer at all times, including when the waist end edge 16 of the backsheet 62 or garment facing portion 3 is pulled away from the wearer facing portion 2 to form the opening 44 and thereby gain access into the openable chassis pocket 5. In addition, as described, a flexible substrate forming the chassis, such as the backsheet 62 and the topsheet 61, may be elasticized or otherwise extensible. Thus, the layered portions of both the topsheet 61 and the backsheet 62 in the openable area along the waist end edge 16 may be elastically contractible, either by means of a waistband 67 or otherwise. In such an embodiment, when the garment facing portion 3 is pulled away for access into the openable chassis pocket 5, the waist end edge 16 of the wearer facing portion 2 may be held elastically against the body of the wearer, thereby facilitating the access, and the opening 44 may also be self-closing by means of the elastic contraction of the waist end edge 16 of the garment facing portion 3 when it is released. In further embodiments, a waist shield may be provided. The waist shield may be used to prevent leakage from the front of the diaper. Generally, the waist shield is provided over the interior of the diaper near the waist end edge and comprises a substantially liquid impervious material.

Method of Manufacturing

In manufacturing an article, such as the diaper 60 of FIGS. 1a-14b, having an openable chassis pocket 5 for receiving a replaceable absorbent core component 30, a wearer facing portion 2 and a garment facing portion 3 may be separately manufactured and then joined together about at least a portion of the peripheries thereof, providing access to the openable chassis pocket 5. Generally, the wearer facing portion 2 includes the topsheet 61 and the garment facing portion 3 includes the backsheet 62. Other layers of the diaper 60 may be allotted between the wearer facing portion 2 and the garment facing portion 3, depending on the desired position of the openable chassis pocket 5 within the layers of the diaper 60 and the absorbent article design itself. Depending on the location of the openable chassis pocket 5 the method of manufacturing may vary. Further, the design of each of the layers, particularly the layers of the absorbent core 10, may vary depending on the respective position of the openable chassis pocket 5 and the position of the layers relative to the other components of the article. While elements of the diaper 60 may be discussed in reference to the method shown in FIGS. 15-20, reference is made to FIGS. 1a-14b for illustration and description of such elements.

In one method of manufacture, illustrated in FIGS. 15-20, the wearer facing portion 2 has a first direction of travel along the article's longitudinal axis 17 and the garment facing portion 3 has a second direction of travel along the article's lateral axis 18. Although the wearer facing portion and the garment facing portion have different directions of travel relative to the article axis, they can have the same geographical direction of travel, e.g. north. In this method of manufacture, the wearer facing portion 2 and the garment facing portion 3 are separately constructed from one or more layers of material.

Figure 15:
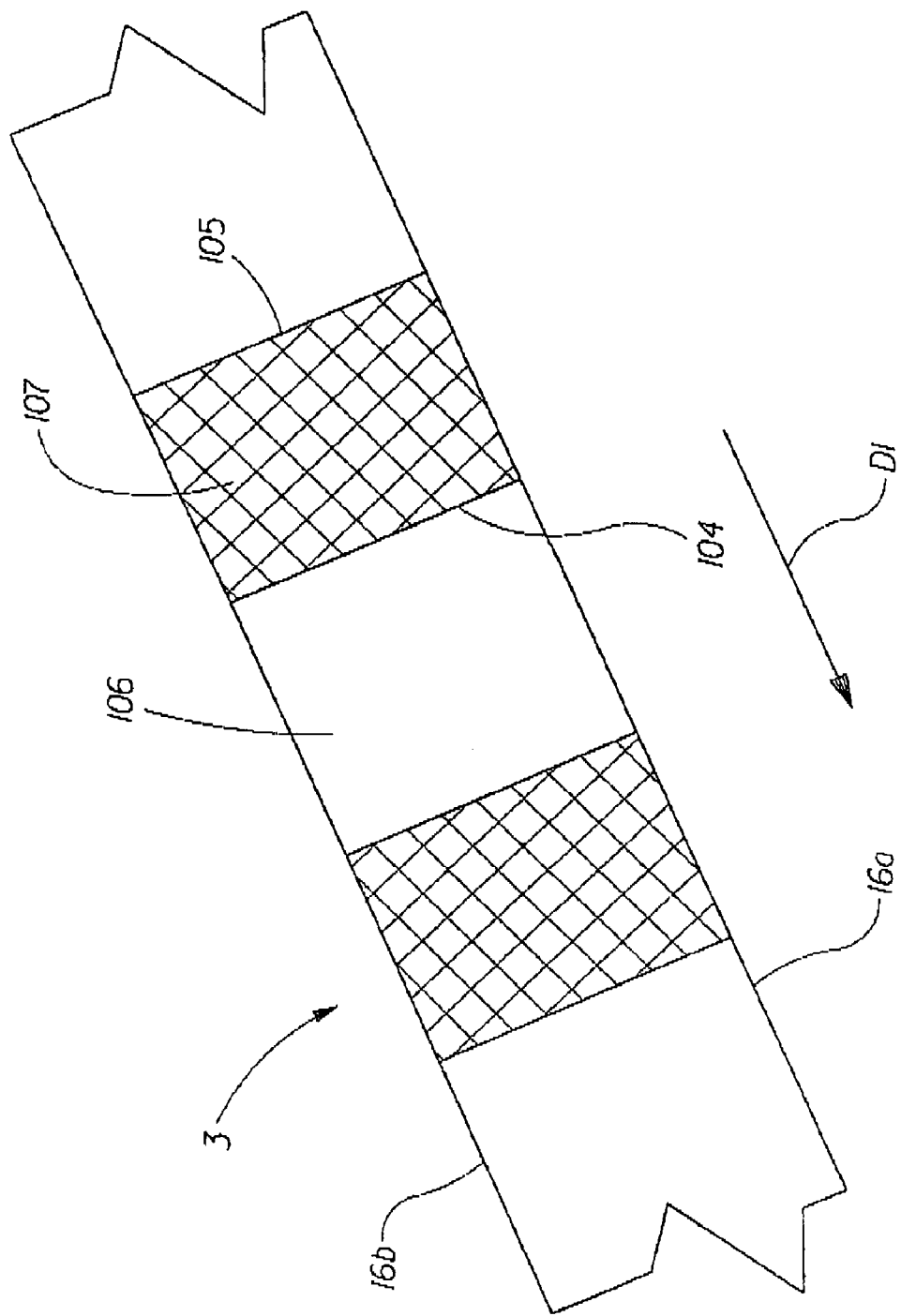
FIG. 15 illustrates a plan view of a process carrier web without a packet in accordance with one embodiment.

FIG. 15 illustrates manufacture of a garment facing portion 3. A generally continuous process carrier web 106 is provided traveling in direction D1. The process carrier web 106 may comprise an extensible non woven web. The garment facing portion 3, comprising the backsheet 62 and the process carrier web 106, may be processed using a machine-direction process or a side-saddle process. In the embodiments of the present invention shown, a side-saddle process is illustrated for processing of the garment facing portion 3. Thus, a first side edge 104 of each article backsheet 62 is processed before a second side edge 105 of the article backsheet 62. Opposing side edges of the process carrier web 106 may correspond with a front waist edge 16a and a rear waist edge 16b of the article. Alternatively, the side edges of the garment facing portion 3 may correspond to the waist edges of the finished article or may be disposed adjacent the waist edges if the side edges of the garment facing portion 3 are folded or trimmed prior to a final product manufacturing step.

During manufacture of the garment facing portion 3, elements of the garment facing portion 3 are built up over the process carrier web. In the embodiment shown, each garment facing portion may comprise a liquid impervious layer 107 such as a poly layer that may be impermeable. The poly layer may be larger than the absorbent core 10 but smaller than the nonwoven portion of the garment facing portion 3 when such a nonwoven is present for example in a laminate structure. The process carrier web 106 comprising at least a portion of the backsheet 62 is conceptually divided along lines to divide the process carrier web into article sections. Individual layers and/or elements of the garment facing portion 3 are placed on and/or are joined to the process carrier web 106.

FIG. 16 illustrates manufacture of a wearer facing portion 2. A generally continuous top carrier web 126 is provided traveling in direction D2. In the embodiment shown, the front waist edge 16a and the rear waist edge 16b of each article are provided along the top carrier web 126. After the wearer facing portion 2 is constructed, the top carrier web 126 is cut into discrete pieces of wearer facing portions. More particularly, the top carrier web 126 is cut along cut lines extending in a direction generally perpendicular to the article's longitudinal axis 17. The cut lines of the web comprising the wearer facing portion may correspond to the front waist edge 16a and back waist edge 16b of the finished article. The discrete wearer facing portions may be held in an elastically extended state and subsequently rotated to align the cut edges with the side edges of the web comprising the garment facing portion. In one embodiment, a portion of the top carrier web 126 may be held by vacuum in its elastically extended configuration and then cut transverse to its direction of travel, i.e. parallel to its lateral axis 18, along cut lines, thereby forming discrete wearer facing portions.

After cutting of the discrete wearer facing portions 2, the wearer facing portions 2 are placed on the garment facing portions 3, as shown in FIG. 17. Thus, FIG. 17 illustrates combining of the wearer facing portions 2 on the garment facing portions 3 on the process carrier web 106. The wearer facing portions 2 are spaced laterally to correspond to the article spacing of the garment facing portion 3. The direction of travel for the discrete wearer facing portion is redirected from the direction of travel of the top carrier web 126 (D2) to the direction of travel of the process carrier web 106 (D1). Suitable means for rotating and aligning one substrate with a second substrate are disclosed in U.S. Pat. Nos. 5,025,910 and 6,604,623, which are herein incorporated by reference. The discrete wearer facing portions 2 are then joined together with the process carrier web 106 the process carrier web 106 is further processed to create an absorbent articles as described in more detail below. After the garment facing portion 3 is joined with the wearer facing portion 2, the composite web undergoes several process transformations including, cutting, folding and seaming in order to form separate absorbent articles as illustrated in FIGS. 16 and 17. As will be described, a film may be provided to form stretchable hip portions or side panels 210 and elastic strands 67a-d may be provided to form waistbands. Cutting may be along cut lines 109 to form leg openings 15 and side edge cut lines 110 to separate the articles.

In an alternative method of manufacture, the wearer facing portion 2 has a first direction of travel along the article's longitudinal axis 17. The garment facing portion 3 has a second direction of travel along the article's lateral axis 18. In accordance with this method, the first direction of travel and the second direction of travel are not the same, geographically. Therefore the direction of travel of one of the portions is disposed at an angle relative to the direction of travel of the other portion. While moving in their respective directions, the wearer facing portion and the garment facing portion are separately constructed from one or more layers of material. Opposing side edges of the web comprising the garment facing portion traveling in the second direction of travel may correspond with a front waist edge and a rear waist edge of the article as described above. After the wearer facing portion 2 is constructed, the top carrier web is moved into position aligning the edges of the process carrier web with the laterally spaced garment facing portions disposed on the process carrier web. The top carrier web is then cut to substantially correspond to the side edges of process carrier web. The direction of travel for the discrete wearer facing portion is redirected from the first direction of travel to the second direction of travel matching the direction of travel of the garment facing potion. Suitable means for introducing and aligning the wearer facing portion and the garment facing portion is disclosed in U.S. Pat. No. 5,693,165, which is herein incorporated by reference. The wearer facing portions are joined together with the garment facing portion, and the web comprising the composite, wearer and garment facing portion, is then further processed to create absorbent articles as described in more detail below.

Generally absorbent articles may be manufactured using an in-line machine-direction process wherein the primary direction of travel is along the longitudinal axis 17 of the article, such as the direction of travel D2 of the top carrier web 126 of FIG. 16. Alternatively absorbent articles may be manufactured using a side-saddle process wherein the primary direction of travel is along the lateral axis 18 of the article, such as the direction of travel D1 of the process carrier web 106 of FIG. 15. In one example of a machine-direction process, the article is processed from a first waist edge to a second waist edge along the longitudinal axis 17. Thus, for example, at a first process, the first waist edge experiences the first process before the second waist edge. In one example of a side-saddle process, the article is processed from a first side edge to a second side edge along the lateral axis 18. Thus, for example, at a first process, the first side edge experiences the first process before the second side edge. As alluded to above in various embodiments, methods for manufacturing an absorbent article having an openable chassis pocket for receiving a replaceable absorbent core component may be manufactured using an in-line machine-direction process, a side-saddle process, or a combination thereof. In one embodiment, such as shown in FIG. 16, the wearer facing portion 2 comprising the topsheet 61 may be processed in a machine direction, with a first waist edge 16a processed before a second waist edge 16b. In alternative embodiments, the second waist edge 16b may be processed before the first waist edge 16a.

With any of the embodiments discussed above, the top carrier web 126 comprising the wearer facing portion 2 is cut into discrete single product units and associated with the garment facing portion 3 disposed on the process carrier web 106 prior to cutting the process carrier web 106 to form separate absorbent articles, such as diaper 60. Generally, if the process carrier web 106 is processed in the side saddle direction, travels in a laterally oriented direction, any portion manufactured in the machine direction, traveling in a longitudinally oriented direction, such as the wearer facing portion 2 in the description above, is rotated ninety degrees prior to association with the garment facing portion 3 disposed on the process carrier web 106. The angle of rotation is determined simply by the angle of one process transformation relative to the other, for example the angle of the wearer facing portion transformation relative to the garment facing portion transformation. The wearer facing portion 2 and the garment facing portion 3 are attached to one another around at least a portion of their periphery, but may remain unsealed along a portion of at least one edge, thereby forming an opening 44 to the openable chassis pocket 5 between the wearer facing portion 2 and the garment facing portion 3. The process carrier web 106 is cut along the cut lines 109, thereby creating the leg openings 15 of the absorbent articles. The process carrier web 106 is folded along the lateral axis 18 aligning its first waist end edge 16a with the longitudinally opposing second waist end edge 16b. Suitable seaming techniques are employed to join the sides of the folded articles comprised within the process carrier web 106. The articles are subsequently cut along the side edge cut lines 110, thereby creating individual absorbent articles.

Figure 18:
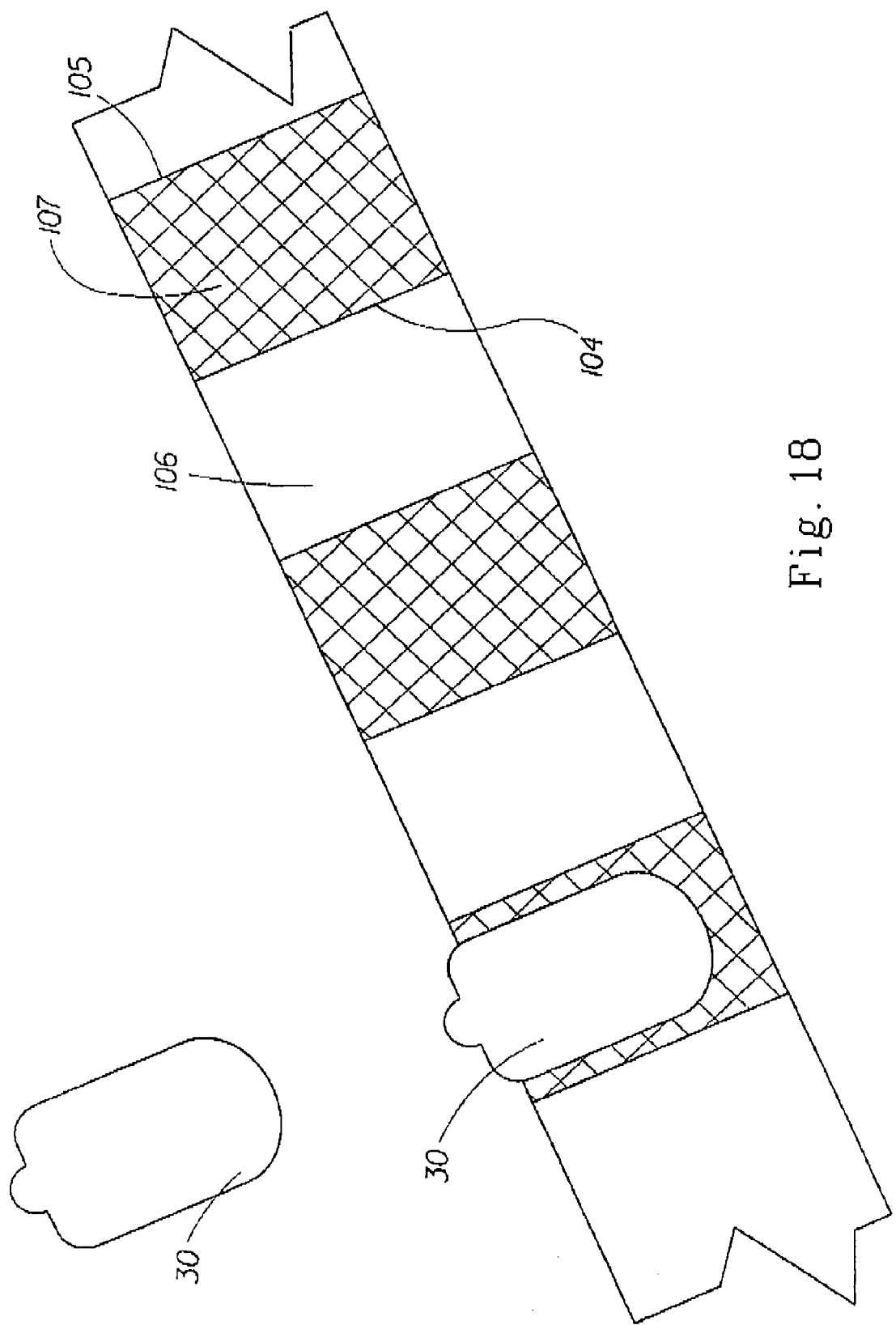
FIG. 18 illustrates a process carrier web with a packet in accordance with one embodiment.

In some embodiments, such as shown in FIGS. 18-20, a replaceable absorbent core component 30 may be provided in the diaper 60 during the manufacture. The removable core component 30, provided as a packet, may be positioned on the process carrier web 106. Where not specifically discussed, reference is made to FIGS. 15-17 for description of like reference numbers. Positioning of the packet may be done at any suitable time. In one embodiment, shown in FIG. 18, the packet is positioned on the process carrier web, for example, on a liquid impervious layer 107 of the garment facing portion 3, prior to combination of the discrete wearer facing portions 2 with the garment facing portions 3. FIG. 19 illustrates processing of the top carrier web 126 to form discrete wearer facing portions 2. FIG. 20 illustrates combination of the discrete wearer facing portions 2 with the garment facing portions of the process carrier web 106.

Whether joined prior to cutting of the garment facing portion 3 or after cutting of the garment facing portion 3, the wearer facing portion 2 and garment facing portion 3 are joined together along at least a portion of the peripheries thereof. In one embodiment, the wearer facing portion 2 and the garment facing portion 3 are joined directly to each other by attachment means such as an adhesive or any other suitable attachment means. For example, a uniform continuous layer of adhesive, a patterned layer of adhesive, or an array of separate lines or spots of adhesive may be used to affix wearer facing portion to the garment facing portion. Adhesives that have been found to be satisfactory are manufactured by Century Adhesives, Inc. of Columbus, Ohio and marketed as Century 5227; and by H. B. Fuller Company of St. Paul, Minn. and marketed as HL-1258. The attachment means may comprise an open pattern network of filaments of adhesive as is disclosed in U.S. Pat. No. 4,573,986. One attachment means of an open pattern network of filaments comprises several lines of adhesive filaments swirled into a spiral pattern such as is illustrated by the apparatus and methods shown in U.S. Pat. Nos. 3,911,173, 4,785,996, and 4,842,666. Alternatively, the attachment means may comprise heat bonds, pressure bonds, ultrasonic bonds, dynamic mechanical bonds, or any other suitable attachment means or combinations of these attachment means.

The topsheet 61 may be provided as part of an extensible web, such as the top carrier web 126. A number of manufacturing techniques may be used to manufacture the topsheet. For example, the topsheet 61 may be formed of woven, nonwoven, spunbonded, carded, or like materials. In nonwoven topsheets, the fibers may be bound together by a thermal binding procedure or by a polymeric binder such as polyacrylate. This sheet is substantially porous and permits a liquid to readily pass therethrough into the underlying absorbent core.

When the topsheet 61 comprises a nonwoven web, the web may be spunbonded, carded, wet laid, melt-blown, hydroentangled, combinations of the above, or the like. The topsheet 61 material generally has little or no affinity for holding aqueous bodily liquids in the area of contact between the topsheet and the wearer's skin. In one embodiment, the topsheet 61 is carded and thermally bonded by means well known to those skilled in the fabrics art. The topsheet 61 may comprise staple length polypropylene fibers having a denier of about 2.2, or any other suitable denier. As used herein, the term "staple length fibers" refers to those fibers having a length of at least about 15.9 mm (0.625 in), or any other suitable length. The topsheet 61 may have a basis weight from about 18 to about 25 $g/m^2$, or any other suitable basis weight. A suitable topsheet is manufactured by Veratec, Inc., a division of International Paper Company, of Walpole, Mass., under the designation P-8. For the purposes of description, a porous web is provided as the topsheet material. In embodiments wherein the topsheet 61 comprises two layers, the second topsheet layer may be adhered to the top carrier web.

At least a portion of the topsheet 61 may be subjected to mechanical stretching in order to provide a "zero strain" stretch laminate that forms at least a portion of the elastic side panels 210. Thus, the topsheet 61 may be elongatable, possibly drawable, but not necessarily elastomeric, so that the topsheet 61 may, upon mechanical stretching, be at least to a degree permanently elongated such that it may not return to its original configuration. The topsheet 61 can be subjected to mechanical stretching without undue rupturing or tearing of the topsheet 61. Thus, in one embodiment, the topsheet 61 has low cross-machine direction (lateral direction) yield strength.

At least a portion of the backsheet 62 may be subjected to mechanical stretching in order to provide both a "zero strain" stretch laminate that forms the elastic side panels 210 and, if desired, to prestrain the portion of the backsheet 62 coinciding with the elastic waist feature or any other elastic feature. Thus, the backsheet 62 may be elongatable, and/or may be drawable, but not necessarily elastomeric, so that the backsheet 62 may, upon mechanical stretching, be at least to a degree permanently elongated such that it may not return to its original undistorted configuration. In some embodiments, the backsheet 62 may be subjected to mechanical stretching without undue rupturing or tearing. Thus, the backsheet 62 may have an ultimate elongation to break of at least about 400% to about 700% in the cross-machine direction as measured using a method consistent with ASTM D-638. The backsheet 62 also may have any other suitable elongation, ranging from 0% to any desired level. Suitable polymeric films for use as the backsheet 62 may contain a high content of linear low density polyethylene. Example materials for the backsheet 62 include blends comprised of about 45-90% linear low density polyethylene and about 10-55% polypropylene, or any other desired composition. Exemplary films for use as the backsheet 62 are manufactured by Tredegar Industries, Inc. of Terre Haute, Ind. under the designations X-8323, RR8220 blend for certain blown films, and RR5475 blend for certain cast films.

As discussed previously, layers of the absorbent article may be allotted between the wearer facing portion 2 and the garment facing portion 3. These layers may include a first absorbent core component 52, a second absorbent core component 51. Generally, an openable chassis pocket 5 is formed between the wearer facing portion 2 and the garment facing portion 3 for receiving a replaceable absorbent core component 20 or 30.

In one embodiment, the absorbent core component 50 is provided with the garment facing portion 3. Thus, the wearer facing portion 2 comprises the topsheet 61 and/or top carrier web 126. More specifically, the top carrier web 126 may act as the topsheet 61. The garment facing portion 3 comprises the process carrier web 106 and the generally impermeable layer forming the backsheet 62 and an absorbent core component 50. A liquid pervious layer, or cover layer, 205 may be provided over the first absorbent core component. The cover layer may be a liquid permeable layer, such as a nonwoven material or tissue that allows fluid to flow to the absorbent core components. The openable chassis pocket 5 is thus provided between the first absorbent core component 52 of the garment facing portion 3 and the wearer facing portion 2.

In another embodiment, the first absorbent core component 52 is provided with the wearer facing portion 2 and the second absorbent core component 51 is provided with the garment facing portion 3. Thus, the wearer facing portion 2 comprises the top carrier web 126, a first absorbent core component 52, and a second liquid permeable layer. The garment facing portion 3 comprises the backsheet 62, including the process carrier web 106 and the poly impermeable layer, and a second absorbent core component 51. A liquid pervious layer, or cover layer, 205 may be provided over the second absorbent core component 51. The cover layer may be a liquid permeable layer, such as a nonwoven material or tissue that allows fluid to flow to the second absorbent core component 51. The openable chassis pocket 5 is thus provided between the second absorbent core component 51 of the garment facing portion 3 and the first absorbent core component 52 of the wearer facing portion 2.

In yet a further embodiment, the absorbent core component 50 is provided with the wearer facing portion 2. Thus, the wearer facing portion 2 comprises the topsheet, an absorbent core component 50 and a liquid pervious layer 205. The garment facing portion 3 comprises the backsheet 62, formed of a generally liquid impermeable layer 107, and the process carrier web 106. The openable chassis pocket 5 is thus provided between the impermeable layer of the backsheet 62 of the garment facing portion 3 and the second absorbent core component 51 of the wearer facing portion 2.

Generally, the openable chassis pocket 5 is adapted for receiving a replaceable absorbent core component 30 and may be provided between any layers of the absorbent article; for example between the topsheet 61 and the backsheet 62, between the topsheet 61 and the absorbent core component 50, between layers of the absorbent core component 50 or between the absorbent core component 50 and the backsheet 62.

Generally, the layers of an absorbent article can be combined in any pattern, and in any sequence, such that an openable chassis pocket 5 is formed. One openable chassis pocket 5 may be formed, or, in other embodiments, two or more openable chassis pockets may be formed. The openable chassis pocket(s) may be formed by combining layers into a preassembled component group (e.g., the wearer facing portion 2, the garment facing portion 3, or other) or alternatively the openable chassis pocket 5 may be formed by attaching a first component group, for example the wearer facing portion 2, to a second component group, for example the garment facing portion 3, in a manner wherein an openable chassis pocket 5 is formed between the two component groups. In one embodiment, each layer of each component group is sealed together. In other embodiments, one or more edges of one or more layers in a given component group are not sealed together. It thus can be seen that, by combining various groupings of layers and partially sealing some layers together, or partially sealing all layers together except for at one or more edges, one or more pockets may be formed during the manufacture of the absorbent article. It also can be seen that, by combining various layer together into a component group and sealing each of the layers of a component group together, and then combining that component group with a similar component group in a manner that does not seal the component groups together around the perimeter, a pocket also may be created. Moreover, any number of component groups may be combined to form any desired number of openable chassis pockets. It also can be seen that the pockets may be oriented in any desired fashion, based on which edges are fastened together and which edges are not fastened together. One or more removable core components 20 and/or 30 may be provided within each of the pockets thus formed.

Other components may be provided on the diaper, as discussed previously. Referring to FIG. 17, waistbands 67 may be applied to the absorbent article, generally over the process carrier web 106. The waistbands may comprise elastic strands 67*a-d*. A film may be provided to form a stretchable hip portion or side panel 210, as shown in FIG. 17. The film may be adhered or laminated to the nonwoven process carrier web 106. The film of the side panels 210 and the elastic strands of the waistbands 67 may be provided in any order. As shown, the elastic strands of the waistbands 67 can be provided substantially continuously over the process carrier web 106 while the film of the side panels 210 is provided at the waist regions of the article. In one embodiment, the film and elastic strands are applied to the garment facing portion 3 of the diaper. Elastic members may be provided on the wearer facing portion 2, as shown in FIG. 19.

Elastic members, film, and/or elastic strands may be secured to the article in an elastically contractible condition so that in a normally unrestrained configuration, the elastic members effectively contract or gather portions of the diaper. The elastic members, film, and/or elastic strands can be secured in an elastically contractible condition in any suitable manner. For example, the elastic members can be stretched and secured while the article is in an extended condition. Any other suitable method also may be used.

The topsheet 61 and the backsheet 62 may have the same size configuration (i.e., are coextensive) such they are joined together about at least a portion of their periphery. The size of the backsheet 62 is dictated in part by the size of the absorbent core and the design selected.

FIGS. 15-20 illustrate manufacture of an absorbent article comprising a wearer facing portion 2 and a garment facing portion 3, the wearer facing portion 2 being built up on a top carrier web 126, the garment facing portion 3 being built up on a process carrier web 106, and the wearer facing portions 2 being combined with the garment facing portions 3 on the process carrier web 106. The absorbent article may comprise side panels 210. The side panels 210 may be mechanically activated, as previously described, to render the side panels 210 elastically extensible. After the articles have been cut, the articles may be folded and seemed along the outer edges of the side panels 210 to form a closed chassis article. Thus, each side panel 210 may be overlapped with and joined to a respective side panel 210 in the opposing waist region. Thus, an absorbent article such as a training pant is formed. Alternatively, the side panels 210 may comprise fastening members that may be used to refastenably join the side panels 210 to one another. In embodiments comprising fastening members, the side panels 210 may be prefastened (fastened prior to packaging) or the article may be packaged with the side panels unfastened.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing an absorbent article, the absorbent article being adapted to be worn about a lower torso of a human body, the absorbent article having a longitudinal axis and a lateral axis and comprising a chassis forming a waist opening and a pair of leg openings and having longitudinally opposing first and second waist end edges, longitudinally opposing first and second waist regions adjacent to respective waist end edges, and a crotch region longitudinally intermediate of the first and second waist regions, the chassis further comprising an openable chassis pocket adapted to receive a replaceable absorbent core component, the method comprising:

advancing a top carrier web in a first direction of travel, wherein the first direction of travel corresponds with the longitudinal axis;

cutting the top carrier web into discrete wearer facing portions, each wearer facing portion including a topsheet;

advancing a process carrier web in a second direction of travel, wherein the second direction of travel corresponds with the lateral axis;

combining components with the process carrier web to a define a continuous length of garment facing portions, each garment facing portion including a backsheet and a first absorbent core component;

redirecting the discrete wearer facing portions from the first direction of travel to the second direction of travel; and combining the discrete wearer facing portions with the continuous length of the garment facing portions, wherein a portion of a periphery of the discrete wearer facing portions remain unattached to the continuous length of garment facing portions, thereby forming an access opening to the openable chassis pocket for receiving the replaceable absorbent core component.

2. The method of claim 1, wherein the openable chassis pocket is at least partially formed between the first absorbent core component and the garment facing portion.

3. The method of claim 1, wherein the openable chassis pocket is at least partially formed between the first absorbent core component and the wearer facing portion.

4. The method of claim 1, wherein the first absorbent core component comprises a plurality of layers of absorbent material.

5. The method of claim 4, wherein the openable chassis pocket is at least partially formed between layers of the first absorbent core component.

6. The method of claim 1, wherein the access opening is located at least one of the first and second waist end edges.

7. The method of claim 1, further comprising the step of disposing the replaceable absorbent core component within the openable chassis pocket.

8. The method of claim 7, wherein a portion of the replaceable absorbent core component extends beyond the first or second waist end edge of the absorbent article.

* * * * *

UNITED STATES PATENT AND TRADEMARK OFFICE
CERTIFICATE OF CORRECTION

| | | |
|---|---|---|
| PATENT NO. | : 7,766,887 B2 | Page 1 of 1 |
| APPLICATION NO. | : 11/598308 | |
| DATED | : August 3, 2010 | |
| INVENTOR(S) | : Burns et al. | |

It is certified that error appears in the above-identified patent and that said Letters Patent is hereby corrected as shown below:

Column 7
Line 63, delete "worm" and insert --worn--.

Signed and Sealed this
First Day of March, 2011

David J. Kappos
*Director of the United States Patent and Trademark Office*